United States Patent [19]
Devlin et al.

[11] Patent Number: 6,146,809
[45] Date of Patent: *Nov. 14, 2000

[54] FLUORESCENT HOST-GUEST-SYSTEM

[75] Inventors: Brian Gerrard Devlin, Takarazuka; Junji Otani, Kobe; Kazuhiko Kunimoto, Takatsuki, all of Japan; Abul Iqbal, Arconciel; Sameer Hosam Eldin, Courtepin, both of Switzerland

[73] Assignee: Ciba Specialty Chemicals Corporation, Tarrytown, N.Y.

[*] Notice: This patent is subject to a terminal disclaimer.

[21] Appl. No.: 09/017,868

[22] Filed: Feb. 3, 1998

[30] Foreign Application Priority Data

| Feb. 3, 1997 | [EP] | European Pat. Off. | 97810049 |
|---|---|---|---|
| Feb. 3, 1997 | [EP] | European Pat. Off. | 97810050 |
| Feb. 3, 1997 | [EP] | European Pat. Off. | 97810051 |
| Feb. 4, 1997 | [EP] | European Pat. Off. | 97810054 |
| Feb. 4, 1997 | [EP] | European Pat. Off. | 97810055 |

[51] Int. Cl.$^7$ .............................. G03C 1/73; G03C 1/76; C08K 5/3445; C09K 11/06; C07D 235/04

[52] U.S. Cl. .................... 430/270.1; 430/286.1; 430/271.1; 430/17; 430/306; 106/494; 252/301.16; 548/301.7

[58] Field of Search ................ 106/494; 430/270.1, 430/17, 271.1, 306, 286.1; 252/301.16; 548/301.7

[56] References Cited

U.S. PATENT DOCUMENTS

| 4,989,956 | 2/1991 | Wu et al. | 349/71 |
|---|---|---|---|
| 5,856,508 | 1/1999 | Jaffe et al. | 548/301.7 |

FOREIGN PATENT DOCUMENTS

| 0456609 | 11/1991 | European Pat. Off. |
|---|---|---|
| 2292947 | 3/1996 | United Kingdom . |
| 9323492 | 11/1993 | WIPO . |
| 9415441 | 7/1994 | WIPO . |

OTHER PUBLICATIONS

J. Appl. Phys., 65(1989) pp. 3610–3616.

J. Phys. Chem., 96 (1992) pp. 1990–1994.

Anal. Biochem., 198, pp. 308–311 (1991).

J. Luminescence, 29; (1984), pp. 309–319.

ACS Symp. Ser. 132, (1980), pp. 39–45, Harris et al.

*Primary Examiner*—Janet Baxter
*Assistant Examiner*—Sin J. Lee
*Attorney, Agent, or Firm*—David R. Crichton; Kevin T. Mansfield

[57] ABSTRACT

Composition comprising a solid organic support material to which either directly or via a bridging group, are covalently linked fluorescent host chromophores and fluorescent guest chromophores, wherein the fluorescence emission spectrum of the host chromophore overlaps with the absorption spectrum of the guest chromophore, wherein the host chromophore is selected from the group consisting of benzo[4,5]imidazo[2,11-a]isoindol-11-ones.

8 Claims, No Drawings

FLUORESCENT HOST-GUEST-SYSTEM

The instant invention relates to a composition comprising a solid organic support material to which either directly or via a bridging group, are covalently linked fluorescent host chromophores and fluorescent guest chromophores, wherein the fluorescence emission spectrum of the host chromophore overlaps with the absorption spectrum of the guest chromophore, wherein the host chromophore is selected from the group consisting of benzo[4,5]imidazo[2,11-a]isoindol-11-ones.

Further, the present invention relates to a process for the preparation of the inventive composition, its use as fluorescent materials, and novel functionalized benzo[4,5]imidazo[2,1-a]isoindol-11-ones, as well.

In EP-A-0 456 609 is disclosed a process for the preparation of 1,2,3,4-tetrachloro-benzo[4,5]imidazo[2,1-a]isoindol-11-one and its derivatives in the presence of selected solvents. These compounds are pigments showing solid state fluorescence and improved outdoor durability. It is also mentioned therein, that the combination of 95% 1,2,3,4-tetrachloro-benzo[4,5]imidazo[2,1-a]isoindol-11-one with 5% of Indanthrone Blue generates a green fluorescent pigment. Such a system is a pigment composite, wherein the new color generated is simply a sum of the two component colors. Hence, the color is not created by virtue of the occurrence of complex, molecular level, energy transfer processes that require close interaction between the components of the mixture.

F. W. Harris et.al. describe in ACS Symp. Ser. 132, 39 (1980) the compound 1,2,3,4-tetra-phenyl-benzo[4,5] imidazo[2,1-a]isoindol-11-one as a model material, as a part of their investigations into phenylated polyimidazopyrrolones for potential use in aerospace applications. However, no reference to its fluorescence behavior is made.

For example, in the area of electroluminescence, Tang et. al. demonstrated the usefulness of sensitized luminescence to create extremely bright electroluminescent devices (J. APPL. PHYS. 65(9), 3610 (1989)).

Also, in the field of biological diagnostics, sensitized luminescence is well established as a ubiquitous and highly sensitive tool to detect specifically targeted biological molecules, such as nucleic acids or antigens e.g. Vener et. al. ANAL. BIOCHEM. 198 (1991) 308–311.

Undertakings by Slobodyanik et. al. (J. LUMINESCENCE 29, 309 (1984)) provide a description of energy transfer between an energy donor and an energy acceptor which are covalently attached to the same polymer.

Studies by Kamachi et. al. (J. PHYS. CHEM. 96(4), 1990 (1992)) demonstrated and discussed energy transfer between two units of a copolymer system.

Brinkley et. al. disclosed polymeric materials that employ sensitized luminescence to detect biological molecules, such as DNA and RNA, and can also be utilized in flow cytometry and analytical microscopy techniques (WO 93/23492). However, only polyazaindacene dyes and coumarin dyes as fluorescent materials are disclosed explicitly for the preparation of fluorescent polymer microparticles. In addition, only the usefulness of fluorescent polymeric beads in biological diagnostics, the possibility to covalently attach the fluorescent moieties to a polymer backbone is pointed-out, further, the opinion is given that this procedure was complicated and unnecessary for such biological applications. Hence, no detailed specific examples of polymer systems that contain host and guest covalently bound to the polymer are disclosed, and no hints are provided to the usefulness of host/guest materials outside the field of specific biological applications.

Hence, the object of the present invention was to provide a composition comprising a solid organic support material to which either directly or via a bridging group, are covalently linked fluorescent host chromophores and fluorescent guest chromophores, wherein the fluorescence emission spectrum of the host chromophore overlaps with the absorption spectrum of the guest chromophore, wherein the host chromophore is selected from the group consisting of benzo[4,5]imidazo[2,11-a]isoindol-11-ones, without the abovementioned disadvantages. Particularly, a composition was to provide wherein a) an intense solid state fluorescence is imparted, preferably wherein the emission wavelengths are in the in the visible region of the electromagnetic spectrum,
b) high ratios of host and guest molecules can be incorporated as part of the polymer whilst retaining solid-state fluorescence properties (i.e. negligible concentration quenching),
c) the material can be excited using wavelengths in both the UV and visible regions,
d) very excellent photostabilities can be achieved,
e) a wide range emission wavelengths can be achieved through selection of guest molecules (color tuning),
f) high thermal stabilities can achieved,
g) soluble and insoluble fluorescent compositions can be generated,
i) migration of fluorescent host and guest molecules is essentially excluded and
l) easy preparation for the materials i.e. single pot reactions is possible.

Accordingly, a composition comprising a solid organic support material to which either directly or via a bridging group, are covalently linked fluorescent host chromophores and fluorescent guest chromophores, wherein the fluorescence emission spectrum of the host chromophore overlaps with the absorption spectrum of the guest chromophore, wherein the host chromophore is selected from the group consisting of benzo[4,5]imidazo[2,11-a]isoindol-11-ones was found.

In addition, a process for the preparation of the inventive composition, its use as fluorescent materials, and novel functionalized benzo[4,5]imidazo[2,1-a]isoindol-11-ones, were found, as well.

The first embodiment of this invention realates to a composition comprising a solid organic support material to which either directly or via a bridging group, are covalently linked fluorescent host chromophores and fluorescent guest chromophores, wherein the fluorescence emission spectrum of the host chromophore overlaps with the absorption spectrum of the guest chromophore, wherein the host chromophore is selected from the group consisting of benzo[4,5]imidazo[2,11-a]isoindol-11-ones.

Under the aspects of the invention host molecule means a fluorescent molecule, preferably selected from the group of solid-state fluorescent organic compounds like dyes, pigments and their derivatives, such that upon exposure to appropriate radiation wavelengths in the UV and or daylight regions they absorb energy. This energy is in turn, preferably almost quantitatively, transferred, in a resonant manner, to the guest chromophore. The host monomer or functionalized host molecule used for the preparation of the compositions according to the invention is preferably sufficiently soluble in a reaction medium, such that it can readily facilitate itself to take part in a fluorescent polymer forming reaction. The reaction medium can be comonomers or an appropriate solvent. A less soluble host monomer can be used, however this may require special apparatus to continuously dissolve the monomer or functionalized molecule into the reaction medium. Solubility may be imparted by the choice of core structures, substituents, functional groups and/or the length of spacers for the functional groups.

Under the aspects of the invention, guest chromophore means fluorescent molecules which possess an absorption region that is at least partially overlapping with the emission region of the respective host in the system. Therein, the guest chromophores accept energy from host molecules, and in turn emit the transferred energy as radiation at wavelengths commensurate to the emission wavelengths of the same guest molecule dissolved molecularly in a solvent. It is further required that the concentration of guest molecules in the composition must be such they do not associate with one another to form localized guest domains, but in fact exist as isolated entities in the polymer bulk, as if they were dissolved molecularly. The guest monomer or functionalized guest molecule used for the preparation of the compositions according to the invention is preferably sufficiently soluble in the reaction medium, such that it can facilitate itself to take part in the fluorescent polymer forming reaction. The reaction medium can be comonomers or an appropriate solvent. Also a less soluble guest monomer can be used but this may require special apparatus to continuously dissolve the monomer or functionalized molecule into the reaction medium. Solubility may be imparted by the choice of core structures, substituents, functional groups and/or the length of spacers for the functional groups.

In accordance with the afore-mentioned descriptions, it is possible for a chromophore to possess the ability to function as either a host or guest compound, in separate systems, provided it meets all the requirements.

The fluorescent composition of the present invention emits solid state fluorescence with a greatly enhanced emission intensity when compared to the solid-state emission intensity of a polymer that contains host units but lacks any guest units, or a polymer that contains guest units but lacks any host units.

The term "enhancement factor" as used herein, can be defined as the increased or decreased factor (as the case can often be), in terms of peak height emission intensities of a solid-state polymer comprising of host and guest fluorescent moieties compared to an identical polymer that does not contain fluorescent guest moieties. Comparisons are considered real, for as long as the excitation radiation wavelengths are identical. Naturally however the emission wavelengths of host/guest material occurs at longer wavelengths (lower energy) as compared to an identical material with no guest component. Enhancement factors for the present invention in general are all positive and preferably should be at least 1.3, more preferably at least 2 and most preferably at least 20.

Further, in the context of this invention, the meaning of the overlap of the absorption spectrum of the guest chromophore with the fluorescence emission spectrum of the host chromophore, is clear to a skilled person in this field. However, to facilitate the understanding to others, overlap means "spectral overlap" defined by the following integral $$S = \int_0^{+\infty} f_F(v) f_A(v) dv$$

wherein $f_F(v)$ is normalized, so that $\int_0^{+\infty} f_F(v) dv$ is equal to fluorescence quantum yield of the host, and where v is the wave number, $f_F$ the fluorescence spectrum of the host measured in quanta, and $f_A$ the spectral distribution of the molar extinction coefficient of the guest. The spectral overlap to realize photoluminescence enhancement usually is greater than 10, preferably greater than 100, more preferably greater than 500. An upper limit makes no sense, because the quantity "overlap" has no maximum (i.e. the larger, the better)).

In the context of this invention, the term "uniform" resp. "uniformly" means that the components (resp. particles) within the matrix i.e. polymer, are evenly, uniformly or homogeneously distributed or dispersed throughout the matrix (polymer matrix), and, preferably in the ideal case are essentially equidistant from each other. According to observations today, the more even or uniform the distribution is, the better are the fluorescence properties, because the coexistence of areas having bright and weak fluorescence are reduced as well as areas wherein the emission color is closer to that of the host than the guest. Furthermore, an uniform or homogeneous or even distribution is preferred, because usually the chances for aggregation are decreased.

In the context of this invention, the term "dissolved" means that a molecule exists as a free and isolated entity in a given matrix, preferably in such a way, that it is disengaged from any interactions between molecules of the same species, i.e. it is entirely surrounded by matrix molecules. Usually the matrix can be a liquid organic solvent or a solid material such as a polymer or another fluorescent material (host), which possesses a different chemical structure, or particles, in which a polymer is dissolved. The concentration limits for molecules in the dissolved state in general depend strongly on the associative nature between the molecule and the matrix medium, and/or the intrinsic cohesive forces that exist between the guest molecules in question. Correspondingly, it is impossible to define universal ranges for preferred concentrations, and therefore, usually must be treated on an ad hoc basis, e.g. by a few simple experiments.

The emission maximum of photoluminescence of the fluorescent polymers of this invention preferably is in the range from about 400 to about 800 nm, more preferably from about 420 to about 780 nm, particularly preferably from about 420 to about 750 nm.

Support material may include for example linear or crosslinked polymers with host and guest structures pendent, or surface modified polymer structures containing host and guest structures pendent on their surface. In principle the composition according to the invention can have two different forms of completion, namely (A) consisting essentially of polymers with host and guest molecules, which are either directly or via a bridging group covalently linked to the polymer backbone, or (B) consisting esssentially of organic support materials to which host and guest molecules are either directly or via a bridging group covalently linked on the surface of said support materials.

The following description first deals with completion form (B), which compared to the completion form (A), possesses the further advantage of reducing the consumption of host and guest molecules, since the host and guest molecules are not located in the interior of an organic particle.

The organic support material of completion form (B) can be opaque, translucent or transparent. Transparent support materials are preferred. Suitable support materials are thermosetting, thermoplastic or structurally crosslinked plastics, glasses, ceramics and minerals. The support materials contain functional groups on the surface for the purpose of linking the host and guest molecules, which, when required may be obtained by a plasma treatment or optionally in a reactive gaseous atmosphere. Preferred support materials are glasses and plastics, for example plastics with functional groups.

The functional groups of the organic support material are preferably selected from the group consisting of amino-, hydroxyl-, thiol-, carboxyl-, $SO_3H$-groups or isocyanate groups. The organic support material may be a polymer that has had its surface modified, for example by plasma treatment, or it may be a natural or synthetic polymer from monomers containing functional groups. Synthetic polymers may also be emulsion polymers and latices comprising of at least one monomer possessing functional groups. Examples of natural polymers are polysaccharides like cellulose, starch or chitosane, which may be partially etherified by $C_1$–$C_4$alkyl or esterified with $C_1$–$C_8$-acyl. Synthetic polymers with functional groups are known and can be prepared by well known methods. Some examples of synthetic polymers are polyvinylalcohol and copolymers of vinyl alcohol with unsubstituted or substituted olefines as comonomers; polymethacrylic acid, polyacrylic acid and polymaleic acid and copolymers of methacrylic acid, acrylic acid and/or maleic acid with unsubstituted or substituted olefines as comonomers; polyhydroxyalkylacrylates, polyhydroxyalkylmetha crylates and polymaleic acid hydroxyalkylesters, and copolymers of hydroxyalkylesters of methacrylic acid, acrylic acid and/or maleic acid with unsubstituted or substituted olefins as comonomers; polyacrylamide and polymethacrylamide and copolymers of acryl amide, methacrylamide or both with unsubstituted or substituted olefins as comonomers; polyaminoalkylacrylates, -methacrylates and -maleic acid esters and copolymers of aminoalkylacrylates, -methacrylates, -maleic acid esters or two or three of these with unsubstituted or substituted olefins as comonomers; polyhydroxyalkyl- or polyaminoalkylvinylalcohol and copolymers of hydroxyalkylvinylether, aminoalkylvinylether or both with unsubstituted or substituted olefins as comonomers; hydroxylated polybutadienes from butadiene, isoprene or chloroprene and copolymers of butadiene, isoprene, chloroprene or two or three of these monomers with unsubstituted or substituted olefins as comonomers; hydroxy- or aminopolystyrene, chlormethylpolystyrene, and polystyrenesulfonic acid and copolymers of hydroxystyrene, aminostyrene, chloromethylstyrene, polystyrenesulfonic acid, or two or more of these monomers with unsubstituted or substituted olefins as comonomers; polyglycidyl ethers and hydroxyalkylated or aminoalkylated polyglycidyl ethers; and polyesters, polyamides and polyurethanes from hydroxyl containing monomers. The support material may also be composed of thermosetting resins, for example epoxy resins, melamine-formaldehyde resins and phenol-form-aldehyde resins. Suitable olefinic comonomers are for example ethene, propene, butene, pentene, octene, vinylchloride, vinylidenechloride, styrenes and acrylonitrile. The support material may also be composed of crosslinked polymers, for example polymerizates with functionalized olefins, optionally nonfunctionalized olefinic monomers, and diolefinic monomers like butadiene, divinylbenzene or dioldiacrylates or diol-dimethacrylates, whereby the olefins may be selected from the above mentioned functional group containing olefins. Further suitable vinyl polymers are polyvinylpyrrolidone, polyvinylimidazole and polyvinylpyridine and copolymers of vinylpyrrolidone, vinylimidazole, vinylpyridine or two or three of them with unsubstituted or substituted olefins as comonomers.

The polymers may be block polymers, alternating polymers, graft polymers or random polymers.

In one embodiment, and a further object of the invention, the composition according to the invention is composed of an organic support material in the form of particles, whereby the host and guest molecules are covalently linked either directly or through a bridging group, to the surface of the particles.

The particles may have an average diameter of 50 nm to 1000 μm, preferably 0.1 to 500 μm, more preferably 0.1 to 200 μm, most preferably 0.1 to 100 μm, and especially preferred 5 to 50 μm. The particles may be round shaped or irregularly shaped, depending on the manufacturing process, and may be compact or porous. The size of the particles are commensurate to the requirements of their final application.

The organic composition may be for example a shaped article from polymers and the like. The size and shape of the article is arbitrary and depends on its final use. These shaped articles are a further preferred embodiment of the invention. The surface of the support material for a shaped article my be smooth or porous. The shaped articles include any composite structures.

The weight average molecular weight of non crosslinked polymers of the present invention usually is in the range from $10^3$ to $2 \times 10^6$, preferably, $10^4$ to $10^6$, more preferably, $2 \times 10^4$ to $10^6$, and most preferably $4 \times 10^4$ to $5 \times 10^5$ gmol$^{-1}$, as for example determined by gel permeation chromatography, using polystyrene standards as calibration.

The amount of host chromophores on the surface is preferably from 0.00001 to 10, more preferably 0.001 to 5, more preferably 0.001 to 3, and most preferably 0.001 to 2 percent by weight, with respect to the total composition.

The amount of guest chromophores is preferably from 0.00001 to 5 percent by weight, more preferably 0.00001 to 3, most preferably 0.00001 to 2, percent by weight, related to the total composition.

The weight ratio of host to guest can be in the range from 50:50 to 9995:5, preferably 6:4 to 999:1 and more preferably 70:30 to 999:1.

The host and guest molecules are advantageously covalently linked to the supporting material through a bridging group. The bridging group may contain 1 to 60 atoms, preferably 1 to 30 atoms, and particularly preferred 1 to 20 atoms, selected from the group consisting of C, O, S and N. The bridging group especially preferred is a hydrocarbon residue, which may be interrupted with one or more and/or end-capped with one of the heteroatoms selected from the group consisting of O, S, N or the group C(O), and which preferably contains in total from 1 to 40 atoms, more preferably 2 to 30 atoms and especially preferred 3 to 20 atoms.

The host and guest molecules covalently linked either directly or through a bridging group to the surface of the support material may be represented by the formulae I and Ia,

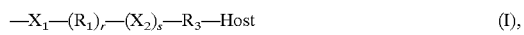

$$—X_1—(R_1)_r—(X_2)_s—R_3—\text{Host} \qquad (I),$$

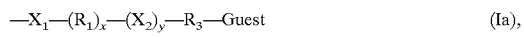

$$—X_1—(R_1)_x—(X_2)_y—R_3—\text{Guest} \qquad (Ia),$$

wherein $X_1$ and $X_2$ each independently from one another mean a direct bond, or $X_1$ and $X_2$ each independently from one another mean —O—, —S—, —$NR_2$—, —C(O)—O—, —O—C(O)—, —O—C(O)—O—, —$SO_2$—O—, —O—$SO_2$—, —O—$SO_2$—O—, —$NR_2$—C(O)—, —C(O)—$NR_2$—, —$NR_2$—C(O)—O—, O—C(O)—$NR_2$—, —$NR_2$—C(O)—$NR_2$—, —$NR_2$—$SO_2$—, —$SO_2$—$NR_2$—, —$NR_2$—$SO_2$—O—, O—$SO_2$—$NR_2$— or —$NR_2$—$SO_2$—$NR_2$— each $R_1$ independently from one another means a bivalent bridging group, Host stands for the monovalent host molecule, Guest stands for a monovalent guest molecule, $R_2$ each independently from one another is H, $C_1$–$C_{12}$alkyl, $C_5$- or $C_6$cycloalkyl, $C_5$- or $C_6$cycloalkylmethyl or -ethyl, phenyl, benzyl or 1-pheny-2-ethyl, $R_3$ each independently from one another are a direct bond, $C_1$–$C_{18}$alkylene, $C_5$- or $C_6$cycloalkylene, $C_6$–$C_{10}$arylene or $C_7$–$C_{12}$aralkylene, r means the numbers 0 or 1 and s means the numbers 0 or 1, with the proviso that s is 0, if r is 0, and x means the numbers 0 or 1 and y means the numbers 0 or 1, with the proviso that y is 0, if x is 0.

In the context of alkyl, $R_2$ has preferably 1 to 6 and especially preferred 1 to 4 C-atoms. Some examples are methyl, ethyl, n- or i-propyl, butyl, pentyl, hexyl and octyl. In the context of cycloalkyl $R_2$ is preferably cyclohexyl, and in the context of cycloalkylmethyl, cyclohexylmethyl is preferred. In a preferred embodiment $R_2$ means H or $C_1$–$C_4$alkyl. The bivalent bridging group is preferably a hydrocarbon residue, which preferably contains 1 to 30, more preferably 2 to 20, most preferably 3 to 20 and particularly preferred 3 to 18 C-atoms, which is unsubstituted or one or more times substituted with $C_1$–$C_4$alkyl, $C_1$–$C_4$alkoxy or =O. The hydrocarbon residue may be also one or more times interrupted with heteroatoms selected from the group consisting of —O—, —S— and —$NR_2$—, whereby $R_2$ is preferably H or $C_1$–$C_4$alkyl.

The bivalent bridging group can be $C_{1-20}$-, preferably $C_2$–$C_{12}$alkylene, which may be linear or branched. Some examples are methylene, ethylene, 1,2- or 1,3-propylene, 1,2-, 1,3- or 1,4-butylene, pentylene, hexylene, octylene, dodecylene, tetradecylene, hexadecylene and octadecylene.

The bivalent bridging group can be polyoxyalkylene with 2 to 12, preferably 2 to 6 and more preferably 2 to 4 oxyalkylene units and 2 to 4, preferably 2 or 3 C-atoms in the alkylene moiety. Especially preferred is polyoxyethylene and polyoxypropylene with 2 to 6 oxyalkylene units.

The bivalent bridging group may be $C_5$–$C_{12}$, preferably $C_5$-$C_8$- and most preferably $C_5$- or $C_6$-cycloalkylene like for example cyclopentylene, cyclohexylene, cyclooctylene or cyclododecylene.

The bivalent bridging group may be $C_5$–$C_{12}$-, preferably $C_5$-$C_8$- and more preferably $C_5$- or $C_6$-cycloalkyl-$C_1$–$C_{12}$-alkylene and most preferably $C_5$- or $C_6$-cycloalkyl-$C_{1-4}$-alkylene. Some examples are -cyclopentyl-$C_nH_{2n}$- and -cyclohexyl-$C_nH_{2n}$-, wherein n means a number of 1 to 4. Especially preferred is -cyclohexyl-$CH_2$-.

The bivalent bridging group may be $C_5$–$C_{12}$-, preferably $C_5$-$C_8$- and more preferably $C_5$- or $C_6$-cycloalkane-($C_1$–$C_{12}$alkylene)$_2$— and most preferably —($C_{1-4}$-alkylene)$_2$. Some examples are cyclopentane-($C_nH_{2n}$-)$_2$ and cyclohexane-($C_nH_{2n}$-)$_2$, wherein n means a number of 1 to 4. Especially preferred is —$CH_2$-cyclohexane-$CH_2$—.

The bivalent bridging group may be $C_6$–$C_{14}$ arylene and preferably $C_6$–$C_{10}$ arylene, for example naphthylene or more preferably phenylene. The bivalent bridging group may be $C_7$–$C_{20}$ aralkylene and preferably $C_7$–$C_{12}$ aralkylene. More preferred is arylene-$C_nH_{2n}$—, wherein arylene means naphthylene and preferably phenylene, and n means a number from 1 to 4. Examples are benzylene and phenylethylene.

The bivalent bridging group may be arene-($C_nH_{2n}$—)$_2$—, wherein arene is preferably naphthalene and more preferably benzene and n is a number from 1 to 4. Examples are xylylene and benzene($CH_2CH_2$)$_2$—.

$R_3$ contains as alkylene preferably 1 to 12 and more preferably 1 to 6 C-atoms. Especially preferred examples are methylene, ethylene, 1,2- or 1,3-propylene and 1,2-, 1,3- and 1,4-butylene. $R_3$ means as arylene preferably phenylene and as aralkylene preferably benzylene.

In a preferred embodiment the bridging group may be selected from the formula Ib —C(O)—O—R'—O—C(O)—(R")—     (Ib)

wherein R' is $C_2$ to $C_{20}$, preferably $C_2$ to $C_{12}$, and more preferably $C_2$ to $C_6$alkylene, phenylene, benzylene, or oligoxyalkylene with preferably 2 to 6, and more preferably 2 to 4 oxyethylene and/or oxypropylene units, and R" means a direct bond, $C_1$ to $C_{12}$alkylene, phenylene or benzylene.

The host molecules are preferably selected from those that possess absorption wavelengths in the range 300 to 700 nm and fluoresce at wavelengths in the range 400 to 780 nm.

The guest molecules are preferably selected from those that posses absorption wavelengths in the range from 380 to 780 nm and fluoresce at wavelengths in the range 400 to 800 nm. It is also preferred that the guest molecules possess fluorescence quantum yields of 0.1 to 1.0, preferably 0.3 to 1.0, more preferably 0.5 to 1.0 and most preferred 0.7 to 1.0.

It is preferred that the solubilities of the host and guest monomer structures are such that they can readily facilitate themselves to solution polymerization or can be readily dissolved in the comonomers of a bulk polymerization mixture. Solvents available for use in solution polymerizations are well known to those familiar in the art.

The guest chromophores used for completion form (B) are preferably monovalent. The guest chromophores can be selected from a broad range of chromophores, so long as they posses fluorescence and an absorption wavelengths, which at least partially overlap, with the emission wavelengths of the host component.

The term guest in formula la is preferably a monovalent residue selected from the group consisting of quinacridones, perylenes, diketopyrrolopyrroles, fluoresceines, rhodamines, coumarines, xanthenes, pyrenes, oxazines, oxazoles, cyanines, phthalocyanines, porphyrines and styryl dyes.

More preferably the guest in formula la is a monovalent residue selected from the group consisting of quinacridones, diketopyrrolopyrroles, rhodamines, and perylenes.

Most preferably the selected guests may be unsubstituted or substituted with halogen like F, Cl, Br, I, —CN, —$NO_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO— or —$SO_2$, $C_3$ to $C_{12}$ cycloalkyl-SO— or —$SO_2$, $C_6$ to $C_{18}$aryl-SO— or —$SO_2$, $C_5$ to $C_{17}$ heteroaryl-SO— or —$SO_2$, $C_3$ to $C_{12}$ cycloalkylalkyl-SO— or —$SO_2$, $C_6$ to $C_{18}$ aralkyl-SO— or —$SO_2$, $C_5$ to $C_{17}$ heteroaralkyl-SO— or —$SO_2$, secundary amino with 2 to 30 carbon atoms, and alkoxyalkyl with 2 to 20 carbon atoms.

The cyclic aliphatic and aromatic residues (substituents) may be also substituted, for example with halogens like F, Cl or Br, —CN, —$NO_2$, $C_1$ to $C_{18}$alkyl, $C_3$ to $C_{12}$ cycloalkyl, $C_6$ to $C_{18}$ aryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy. The substituent alkyl may be linear or branched and may be substituted with halogens like F or Cl.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl- SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

The number of substituents is arbitrary and depends essentially upon synthetic possibilities and the desired optical properties related to fluorescence and absorption.

Preferably the term guest in formula Ia is selected from the group consisting of monovalent residues of formulae;

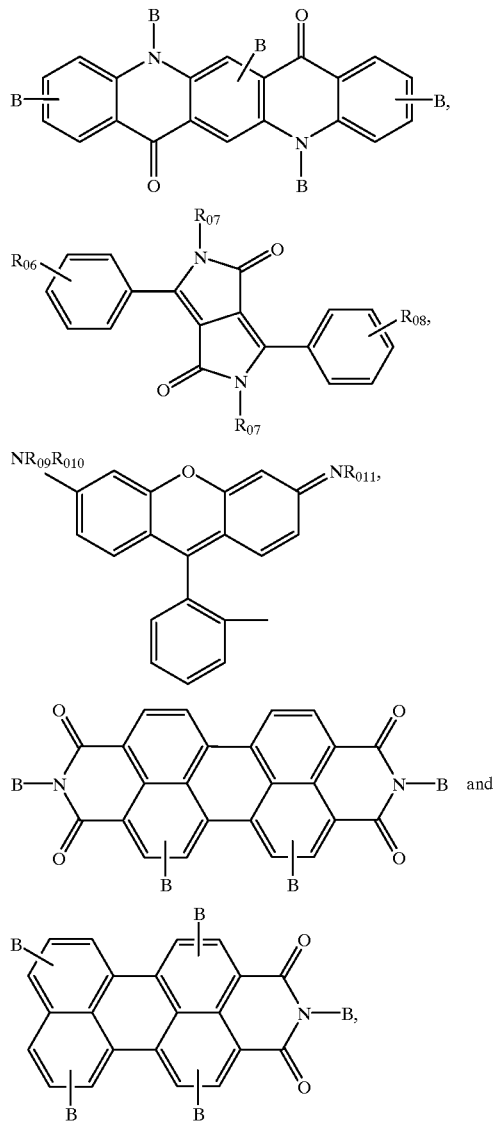

and salts of the rhodamine residue, inclusive salts with the group $=N^+ R_{O11}R_{O12}$, wherein $R_{O6}$ is a bond and both $R_{O7}$ and $R_{O8}$ or independently H or a substituent, or one of $R_{O7}$ is H and the other $R_{O7}$, $R_{O6}$ and $R_{O8}$ are independently H or a substituent, or $R_{O8}$ is a bond and the other $R_{O7}$ and $R_{O6}$ are independently H or a substituent, one of B is a bond and the others are H or a substituent, $R_{O11}$, means $C_1$ to $C_{20}$alkyl, or phenyl or benzyl which are unsubstituted or substituted with $C_1$ to $C_{18}$alkyl, $R_{O9}$ and $R_{O10}$ independently of one another mean H, $C_1$ to $C_{20}$alkyl, or phenyl or benzyl which are unsubstituted or substituted with $C_1$ to $C_{18}$ alkyl, $R_{O12}$ is H or $C_1$ to $C_{18}$ alkyl, whereby the rings are unsubstituted or substituted with F, Cl, Br, 1, —CN, —NO$_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_8$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO— or —SO$_2$, $C_3$ to $C_{12}$ cycloalkyl-SO— or —SO$_2$, $C_6$ to $C_{18}$ aryl-SO— or —SO$_2$, $C_5$ to $C_{17}$ heteroaryl-SO— or —SO$_2$, $C_3$ to $C_{12}$ cycloalkylalkyl-SO— or —SO$_2$, $C_6$ to $C_{18}$ aralkyl-SO— or —SO$_2$, $C_5$ to $C_{17}$ heteroaralkyl-SO— or —SO$_2$, secundary amino with 2 to 30 carbon atoms, and alkoxyalkyl with 2 to 20 carbon atoms.

The cyclic aliphatic and aromatic residues may be also substituted, for example with F, Cl, Br, I, —CN, —NO$_2$, $C_1$ to $C_{18}$ alkyl, $C_3$ to $C_{12}$ cycloalkyl, $C_6$ to $C_{18}$ aryl, , $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy. The alkyl may be substituted with halogen like F, Cl or Br.

More preferred substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

$R_{11}$ means preferably $C_1$ to $C_{18}$ alkyl, which may linear or branched, or phenyl or benzyl which are unsubstituted or substituted with $C_1$ to $C_{12}$alkyl, and $R_{O9}$ and $R_{O10}$ independently of one another mean preferably H, $C_1$ to $C_{18}$ alkyl, or phenyl or benzyl which are unsubstituted or substituted with $C_1$ to $C_{12}$ alkyl. Examples are methyl, ethyl, and the isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, phenyl, benzyl, methylphenyl, ethylphenyl, propylphenyl, butylphenyl, pentylphenyl, hexylphenyl, heptylphenyl, octylphenyl, methylbenzyl, ethylbenzyl, propylbenzyl, butylbenzyl, pentylbenzyl, hexylbenzyl, heptylbenzyl, and octylbenzyl.

$R_{O12}$ means preferably $C_1$ to $C_{12}$ alkyl, more preferably $C_1$ to $C_8$ alkyl and most preferably $C_1$ to $C_4$ alkyl.

Suitable salts may be derived from inorganic or organic acids, for example HCl, HBr, H$_2$SO$_4$, carboxylic acids like acetic acid, chloro- or fluoroacetic acids, propionic acid, benzoic acid, chloro- or fluorobenzoic acids, sulfonic acids like methylsulfonic acid, chloro- or fluoromethylsulfonic acids, phenylsulfonic acid, toluylsulfonic acid, and chloro- or fluorobenzenesulfonic acids.

More preferred guest moieties of the formula la are residues of the following formulae:

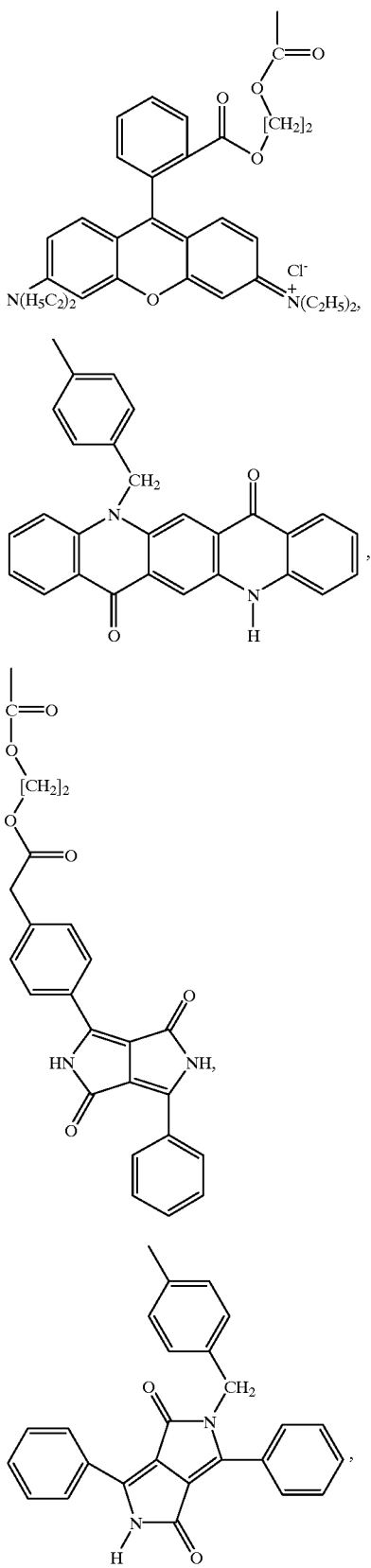

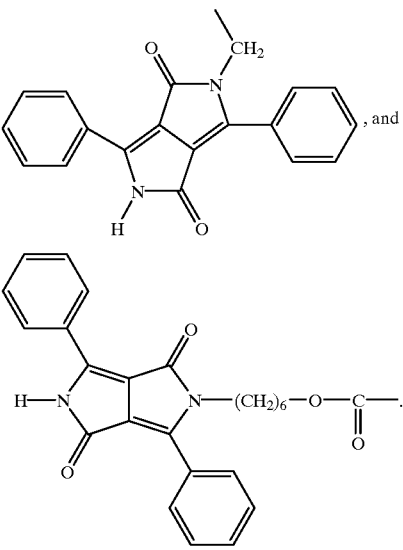

The host chromophores used for completion form (B) are preferably monovalent. The host chromophores can be selected from a broad range of chromophores, so long as they emit solid-state fluorescence, and that their emission wavelengths are at least partially overlapping with the absorption range of the corresponding guest in the system.

The monovalent host residues in formula I may be unsubstituted or substituted with F, Cl, Br, I, —CN, —NO$_2$, C$_1$ to C$_{18}$ alkyl, C$_3$ to C$_{12}$ cycloalkyl, C$_6$ to C$_{18}$ aryl, C$_5$ to C$_{17}$ heteroaryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy, C$_5$ to C$_{17}$ heteroaryloxy, C$_3$ to C$_{12}$ cycloalkylalkyloxy, C$_6$ to C$_{18}$ aralkyloxy, C$_5$ to C$_{17}$ heteroaralkyloxy, C$_1$ to C$_{18}$ alkylthio, C$_3$ to C$_{12}$ cycloalkylthio, C$_6$ to C$_{18}$ arylthio, C$_5$ to C$_{17}$ heteroarylthio, C$_3$ to C$_{12}$ cycloalkylalkylthio, C$_6$ to C$_{18}$ aralkylthio, C$_5$ to C$_{17}$ heteroaralkylthio, C$_1$ to C$_{18}$ alkyl-SO— or —SO$_2$, C$_3$ to C$_{12}$ cycloalkyl-SO— or —SO$_2$, C$_6$ to C$_{18}$ aryl-SO— or —SO$_2$, C$_5$ to C$_{17}$ heteroaryl-SO— or —SO$_2$, C$_3$ to C$_{12}$ cycloalkylalkyl-SO — or —SO$_2$, C$_6$ to C$_{18}$ aralkyl-SO— or —SO$_2$, C$_5$ to C$_{17}$ heteroaralkyl-SO— or —SO$_2$, secunary amino with 2 to 30 carbon atoms, and alkoxyalkyl with 2 to 20 carbon atoms.

The cyclic aliphatic and aromatic residues (substituents) may be also substituted, for example with F, Cl, Br, I, —CN, —NO$_2$, C$_1$ to C$_{18}$ alkyl, C$_3$ to C$_{12}$ cycloalkyl, C$_6$ to C$_{18}$ aryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy. The substituent alkyl may be linear or branched and may be substituted with a halogen like F or Cl.

Examples of substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

The number of substituents is arbitrary and depends essentially upon synthetic possibilities and the desired optical properties pertaining to fluorescence and absorption.

Especially preferred monovalent host residues are derived from benzo[4,5]imidazo[2,1-a]isoindol-11-ones.

The benzo[4,5]imidazo[2,1-a]isoindol-11-ones used in completion form (B) are preferably monovalent residues and may be selected from the formulae II and IIa,

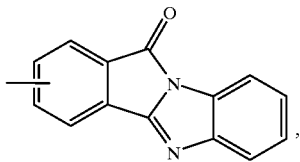
(II)

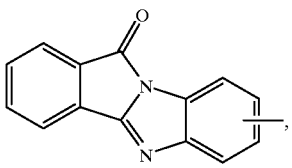
(IIa)

wherein
neighboring carbon atoms of the benzene rings can be condensed with benzene rings, heteroaromatic rings or both, and to these rings can be linked the free bond rather than to benzene rings of the core polycyclic structure, the aromatic rings are unsubstituted or substituted with F, Cl or Br, I, —CN, —NO$_2$, C$_1$ to C$_{18}$ alkyl, C$_3$ to C$_{12}$ cycloalkyl, C$_6$ to C$_{18}$ aryl, C$_5$ to C$_{17}$ heteroaryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy, C$_5$ to C$_{17}$ heteroaryloxy, C$_3$ to C$_{12}$ cycloalkylalkyloxy, C$_6$ to C$_{18}$ aralkyloxy, C$_5$ to C$_{17}$ heteroaralkyloxy, C$_1$ to C$_{18}$ alkylthio, C$_3$ to C$_{12}$ cycloalkylthio, C$_6$ to C$_{18}$ arylthio, C$_5$ to C$_{17}$ heteroarylthio, C$_3$ to C$_{12}$ cycloalkylalkylthio, C$_6$ to C$_{18}$ aralkylthio, C$_5$ to C$_{17}$ heteroaralkylthio, C$_1$ to C$_{18}$ alkyl-SO— or —SO$_2$, C$_3$ to C$_{12}$ cycloalkyl-SO— or —SO$_2$, C$_6$ to C$_{18}$ aryl-SO— or —SO$_2$, C$_5$ to C$_{17}$ heteroaryl-SO— or —SO$_2$, C$_3$ to C$_{12}$ cycloalkylalkyl-SO— or —SO$_2$, C$_6$ to C$_{18}$ aralkyl-SO— or —SO$_2$, C$_5$ to C$_{17}$ heteroaralkyl-SO— or —SO$_2$, secunary amino with 2 to 30 carbon atoms, and alkoxyalkyl with 2 to 20 carbon atoms. The cyclic aliphatic and aromatic residues may be also substituted, for example with F, Cl, Br, 1, —CN, —NO$_2$, C$_1$ to C$_{18}$ alkyl, C$_3$ to C$_{12}$ cycloalkyl, C$_6$ to C$_{18}$ aryl, , C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy, C$_3$ to C$_{12}$ cycloalkyloxy, C$_6$ to C$_{18}$ aryloxy.

The cyclic aliphatic and aromatic residues (substituents) may be also substituted, for example with halogens like F, Cl or Br; or —CN, —NO$_2$, C$_1$ to C$_{18}$ alkyl, C$_3$ to C$_{12}$ cycloalkyl, C$_6$ to C$_{18}$ aryl, C$_3$ to C$_{12}$ cycloalkylalkyl, C$_6$ to C$_{18}$ aralkyl, C$_5$ to C$_{17}$ heteroaralkyl, C$_1$ to C$_{18}$ alkyloxy C$_3$ to C$_{12}$cycloalkyloxy, C$_6$ to C$_{18}$aryloxy. The substituent alkyl may be linear or branched and may be substituted with halogen like F or Cl.

Examples of substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 or 2 rings are condensed with the neighboring carbon atoms to form bicyclic or tricyclic systems. They may be selected from benzene, furan, thiophene, pyrrole, pyridine, and pyrimidine.

In a preferred embodiment the monovalent host residues correspond to formulae IIb and IIc,

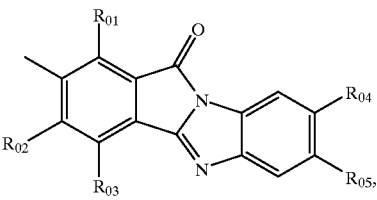
(IIb)

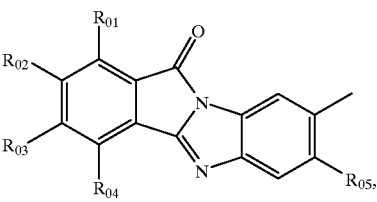
(IIc)

wherein
R$_{01}$, R$_{02}$, R$_{03}$, R$_{04}$, and R$_{05}$ independently from one another mean H, Cl, C$_1$ to C$_{18}$ alkyl, C$_1$ to C$_{18}$ alkoxy, phenyl, benzyl, C$_1$ to C$_{12}$ alkylphenyl or C$_1$ to C$_{12}$ alkylbenzyl. R$_{05}$ in formula IIc means preferably H. R$_{01}$, R$_{02}$, R$_{03}$ and R$_{04}$ are especially preferred H, phenyl, benzyl, C$_1$ to C$_{12}$ alkylphenyl or C$_1$ to C$_{12}$ alkylbenzyl and R$_{05}$ is especially preferred H.

Some preferred examples of host chromophores corresponding to formula I are

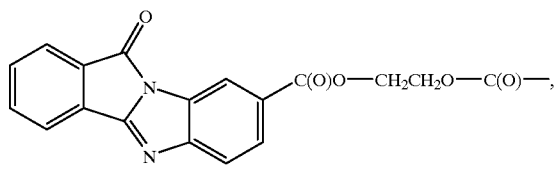

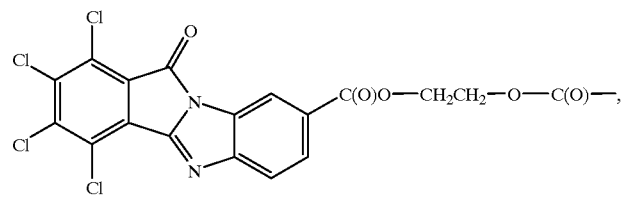

-continued

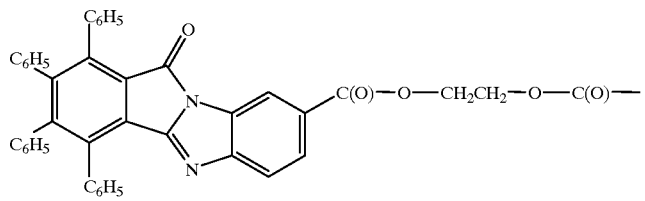

and

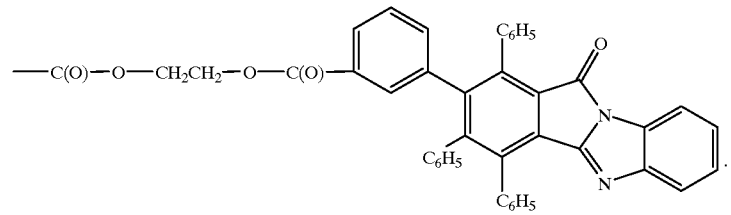

The composition according to completion form B may be prepared according to well known immobilization methods. A further preferred embodiment of the invention is a process for the preparation of the composition according to completion form B, characterized in that an inorganic or organic support material, containing functional groups on the surface, is reacted with functionalized fluorescent guest chromophores and functionalized fluorescent host chromophores either simultaneously or in a two step reaction.

The reaction may be carried-out by dissolving the functional host and guest compounds in an inert solvent, adding a support material and reacting the mixture at suitable temperatures, for example 0 to 200° C. and preferably 20 to 150° C. Suitable solvents are described later. The isolation is carried-out by known filtration methods, and the material may be purified by washing and finally it may be dried.

The immobilization and the synthesis of bridging groups can be carried out according to methods well known in the art and are well documented in the literature. In principle it is possible to convert one functional group into another functional group, for example —$CH_2OH$— groups through oxidation into carboxylic acids, carboxylic acids into amides or carboxylic acids into halogenides, amine groups into isocyanate groups, alcohols or amines into carbonates or urethanes. It is also possible, to react alcohols or amines with halogen carboxylic acids (for example monochloro acetic acid or chloromethylbenzoic acid which may then be linked to hydroxyl or amino groups). It is further possible to carry out chain extensions with di-functional agents like epoxides, azirines, diols, diamines, dicarboxylic acids or -esters and diisocyanates. Reactions using di-functional agents can be single-step or multi-step, depending on the degree of chain length desired. The bridging groups may be introduced through the functional groups of the support material or the functional groups of the host and guest compounds.

In a preferred embodiment and further object of the invention (completion form (A)), the composition according to the invention, comprises, as a support material, a polymer backbone to which, either directly or via a bridging groups, fluorescent host molecules and fluorescent guest chromophores are covalently linked, wherein the fluorescence excitation wavelengths of the host at least partially overlaps the absorption wavelengths of the guest.

For the host and guest compounds, as well as the bridging groups, the accomplishments and preferred embodiments described for completion form (B) are considered to apply to completion form (A).

The preparation of polymers and their immobilization is well known in the art. In principle two procedures may be used. In a first aspect it is possible to polymerize monomers with pendent host and guest molecules. In a second aspect it is possible to use polymers with pendent functional groups and to react them with host and guest molecules containing functional groups.

The host and guest compounds are linked through functional groups bonded to structural units of the backbone. Examples of functional groups are —OH, —SH, —$NH_2$, —$NHR_2$, —CH =O, carboxylic acid, —$SO_3H$, epoxide, vinyl or isocyanate, wherein $R_2$ is preferably H or $C_1$ to $C_4$ alkyl.

The polymers can be selected from natural or synthetic polymers. Examples of natural polymers are polysaccharides like cellulose, starch or chitosane, which may be partially etherified by $C_1$–$C_4$alkyl or esterified with $C_1$–$C_8$ acyl. Synthetic polymers with functional groups can be prepared in accordance with well known methods. Some examples of synthetic polymers are polyvinylalcohol and copolymers of vinyl alcohol with unsubstituted or substituted olefines as comonomers; polymethacrylic acid, polyacrylic acid and polymaleic acid and copolymers of methacrylic acid, acrylic acid and/or maleic acid with unsubstituted or substituted olefines as comonomers; polyhydroxyalkylacrylates, polyhydroxyalkylmethacrylates and polymaleic acid hydroxyalkylesters, and copolymers of hydroxyalkylesters of methacrylic acid, acrylic acid and/or maleic acid with unsubstituted or substituted olefins as comonomers; polyacrylamide and polymethacrylamide and copolymers of acryl amide, methamonomers; crylamide or both with unsubstituted or substituted olefins as comonomers; polyaminoalkyl-acrylates, -methacrylates and -maleic acid esters and copolymers of aminoalkylacrylates, -methacrylates, -maleic acid esters or two or three of these with unsubstituted or substituted olefins as comonomers; polyhydroxyalkyl- or polyaminoalkylvinylalcohol and copolymers of hydroxyalkylvinylether, aminoalkylvinylether or both with unsubstituted or substituted olefins as comonomers; hydroxylated polybutadienes from butadiene, isoprene or chloroprene and copolymers of butadiene, isoprene, chloroprene or two or three of these monomers with unsubstituted or substituted olefins as comonomers; hydroxy- or aminopolystyrene, chlormethylpolystyrene, and polystyrenesulfonic acid and copolymers of hydroxystyrene, aminostyrene, chloromethylstyrene, polystyrenesulfonic acid, or two or more of these monomers with unsubstituted or substituted olefins as comonomers; polyglycidyl ethers and hydroxyalkylated or aminoalkylated polyglycidyl ethers; and polyesters, polyamides and polyurethanes from hydroxylic group containing monomers. The polymer may also be composed of thermosetting resins, for example epoxide resins, melamine-formaldehyde resins and phenol-form-aldehyde resins. Suitable olefinic comonomers are for example ethene, propene, butene, pentene, octene, vinylchloride, vinylidenechloride, styrenes and acrylonitrile. Further suitable vinyl polymers are polyvinylpyrrolidone, polyvinylimidazole and polyvinylpyridine and copolymers of vinylpyrrolidone, vinylimidazole, vinylpyridine or two or three of them together with unsubstituted or substituted olefins as comonomers.

The polymer may also be composed of crosslinked polymers, for example polymerisates with functionalized olefins, optionally nonfunctionalized olefinic monomers, and di-olefinic monomers like butadiene, divinylbenzene or dioldiacrylates or dioldimethacrylates.

A weight average molecular weight of the polymer of the present invention can be in the range from $10^3$ to $2\times10^6$, preferably, $10^4$ to $10^6$, more preferably, $2\times10^4$ to $10^6$, and most preferably $4\times10^4$ to $5\times10^5$ gmol$^{-1}$, as determined by gel permeation chromatography, using polystyrene standards as calibration.

The weight ratio of host to guest structural units can be in the range from 50:50 to 9995:5, preferably 6:4 to 999:1 and more preferably 70:30 to 999:1. The weight ratio of (host structural units plus guest structural units):non-fluorescent structural units is dependent on the actual practical application, hence there are no well defined preferred ratios, other than the broad range 100:0 to 1:999. In certain applications where both color strength and fluorescence are required, then the preferred ratios of chromophore structural units to non-fluorescent structural units are 20:80 to 100:0, preferably 50:50 to 100:0 and more preferably 80:20 to 100:0. In circumstances where fluorescence is desired but color strength is not required, then the preferred ratio of chromophore structural units to non-fluorescent structural units are 20:80 to 1:999, more preferably 10:90 to 1:999 and more preferably 5:95 to 1:999.

In one embodiment of the polymeric composition of the invention and as a further object of the invention, the polymer can be in the form of particles, which may be obtained by milling polymers or by emulsion polymerizations.

The particles may have an average diameter of 50 nm to 1000 μm, preferably 0.1 to 500 μm, more preferably 0.1 to 200 μm, most preferably 0.1 to 100 μm, and especially preferred 5 to 50 μm. The particles may be round shaped or irregularly shaped, depending on the manufacturing process, and the particles may be compact or porous. The sizes of the particles are commensurate to the requirements of their final application.

The host and guest molecules linked to the polymers may be derived from mono-functional or polyfunctional host and guest molecules. Preferably the molecules are mono- to trifunctional, especially preferred are mono- or difunctional.

The polymer may be composed from monomeric units with covalently linked monovalent and/or divalent residues of a host molecule and from monomeric units with covalently linked monovalent and/or divalent residues of a guest molecule, and optionally from other comonomeric units.

The monomeric units containing the host (designated as k) may be present in the broad range from 0.0005 to 0.9995. In certain applications where both color strength and fluorescence are required, then the preferred ratios of host chromophore structural units to non-fluorescent structural units are 0.2 to 0.9995. In applications where fluorescence is desired but color strength is not required, then the preferred ratio of host chromophore structural units is 0.05 to 0.2.

The monomeric units containing the guest (designated as m) are preferably present in the range from 0.0005 to 0.5, more preferably 0.001 to 0.2, and most preferably 0.001 to 0.05. Non-fluorescent monomeric units (designated as n) is in the broad range of 0 to 0.999. In applications where both color strength and fluorescence are required, then the preferred ratio of non-fluorescent structural units is 0.0005 to 0.2. In applications where fluorescence is desired but color strength is not required, then the preferred ratio of non-fluorescent structural units is 0.8 to 0.9995, whereby k, m and n are typically selected such as to satisfy k+m +n=1.

The polymers may be composed of recurring structural units of formula III and recurring structural units of formula IIIa,

(III)

(IIIa)

or may be composed of recurring crosslinking units of formulae IIIb or IIIc, alone or in combination with one or both of the structural units of formulae III and IIIa,

(IIIb)

(IIIc)

wherein

A is a trivalent organic residue, $A_1$ is the same or a different trivalent residue from the group of A, $A_2$ is a trivalent organic residue, $A_3$ is a trivalent organic residue from the group of $A_2$, Host is a monovalent or divalent fluorescent host chromophore, as defined before, which is covalently linked, either directly or via a bridging group, and Guest, is a monovalent or divalent fluorescent guest chromophore, as defined before, which is covalently linked, either directly or via a bridging group, wherein the fluorescence excitation wavelengths of the host are at least partially overlapped by the absorption wavelengths of the guest, whereby A and $A_1$ are copolymerisable, $A_2$ and $A_3$ are copolymerizable, and A and $A_1$ are copolymerizable with $A_2$, $A_3$ or both, when used in combination.

The polymer may additionally contain structural units of formula IIId,

(IIId), wherein $A_4$ means the same or a different divalent residue which is copolymerizable with A to $A_3$.

A, $A_1$, $A_2$, $A_3$, and A4 may be derived from monomers selected from the group consisting of olefins, polyolefines like di- or triolefines, polyalcohols like diols and triols, polyamines like diamines and triamines, polyisocyanates like di- or triisocyanates, polycarboxylic acids like di- and tricaboxylic acids, and polyepoxides like di- and triepoxides.

The weight ratio of structural elements of formula III, or IIIb, resp., to other structural units is dependent on the actual practical application, hence there are no well defined preferred ratios, other than the broad range 9995:5 to 5:9995. In certain applications where both color strength and fluorescence are required, then the preferred ratios of structural units III to other structural units is 20:80 to 9995:5, preferably 50:50 to 9995:5 and more preferably 80:20 to 9995:5. In circumstances where fluorescence is desired but color strength is not required, then the preferred ratio of chromophore structural units to non-fluorescent structural units is 20:80 to 5:9995, more preferably 10:90 to 5:9995 and more preferably 5:95 to 5:9995.

The amount of guest is system dependent, hence there is no well defined ratios. In general the structural elements of formula IIIa, or IIIc, resp., may be present in an amount of 0.05 to 50 weight %, preferably 0.1 to 5 weight %, more preferably 0.1 to 5 weight %, most preferably 0.1 to 3 weight % of the polymer.

In a preferred embodiment the polymers according to the invention contain recurring structural units of formula IV, recurring structural units of formula IVa, and optionally recurring structural units of formula V,

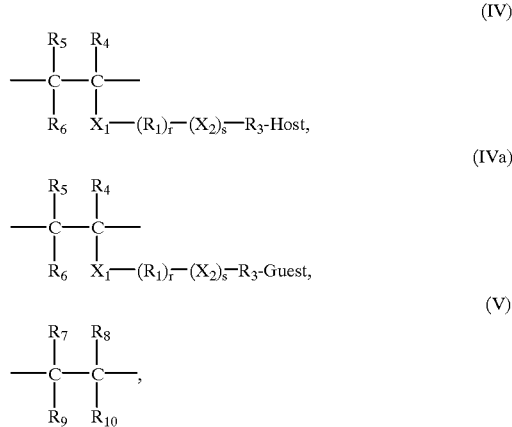

wherein
$X_1$ and $X_2$ each independently of one another mean a direct bond, or $X_1$ and $X_2$ each independently of one another mean —O—, —S—, —NR$_2$—, —C(O)—O—, —O—C(O)—, —O—C(O)—O—, —SO$_2$—O—, —O—SO$_2$—, —O—SO$_2$—O—, —NR$_2$—C(O)—, —C(O)—NR$_2$—, —NR$_2$—C(O)—O—, O—C(O)—NR$_2$—, NR$_2$—C(O)—NR$_2$—, —NR$_2$—SO$_2$—, —SO$_2$—NR$_2$—, —NR$_2$—SO$_2$—O—, —O—SO$_2$—NR$_2$—, $R_1$ means a bivalent bridging group,
Guest means a monovalent fluorescent guest chromophore,
Host means a monovalent fluorescent host, wherein its fluorescence emission wavelengths at least partially overlap with the absorption wavelengths of the guest,
$R_2$ means H, $C_1$–$C_{12}$ alkyl, $C_5$- or $C_6$ cycloalkyl, $C_5$- or $C_6$ cycloalkylmethyl or -ethyl, phenyl, benzyl or 1-phenyl-2-ethyl,
$R_3$ means a direct bond, $C_1$–$C_{18}$ alkylene, $C_5$- or $C_6$-cycloalkylene, $C_6$–$C_{10}$ arylene or $C_7$–$C_{12}$ aralkylene,
r each independently of one another mean the numbers 0 or 1 and the s each independently of one another mean the numbers 0 or 1, with the proviso that if s is 0, r is 0,
$R_4$ and $R_5$ each independently of one another mean H, $C_1$–$C_6$alkyl, $C_6$–$C_{10}$aryl or $C_7$–$C_{12}$ aralkyl,
$R_6$ means H or the group —C(O)O—$R_{11}$,
$R_7$ means H, $C_1$–$C_6$alkyl, $C_6$–$C_{10}$aryl or $C_7$–$C_{12}$aralkyl,
$R_8$ means H, F, Cl, CN, $C_1$–$C_6$alkyl or $C_6$–$C_{10}$aryl,
$R_9$ means H, $C_1$–$C_6$alkyl or —C(O)O—$R_{11}$,
$R_{10}$ means H, $C_1$–$C_6$ alkyl, $C_6$–$C_{10}$ aryl, $C_7$–$C_{12}$ aralkyl, imidazolyl, pyrrolidonyl, group —$X_1$—$(R_1)_r$—$(X_2)_s$—H, and
$R_{11}$ means H, K, Na, $C_1$–$C_{18}$ alkyl, $C_1$–$C_{18}$ hydroxyalkyl, cyclohexyl, cyclopentyl, cyclohexylmethyl, phenyl, $C_1$–$C_4$alkylphenyl, benzyl or $C_1$–$C_4$ alkylbenzyl.

For $X_1$, $X_2$, $R_1$, $R_2$, $R_3$, r, s, Host and Guest the meanings and preferred embodiments as described before for completion form (B) are also valid for completion form (A).

$R_4$ and Rs as alkyl mean preferably $C_1$–$C_4$ alkyl, for example methyl, ethyl, n- or i-propyl and n-, i- or t-butyl; as aryl preferably naphthyl or phenyl; and as aralkyl preferably benzyl. Especially preferred $R_4$ is H and $R_5$ is H or methyl.

$R_6$ means preferably H, —C(O)OH or —C(O)O—$C_1$ to $C_4$-alkyl.

$R_7$ means as alkyl preferably $C_1$ to $C_4$alkyl, for example methyl, ethyl, n- or i-propyl, and n-, i- or t-butyl; as aryl preferably naphthyl or phenyl and as aralkyl preferably benzyl. Especially preferred $R_7$ is H.

for alkyl $R_8$ means preferably $C_1$ to $C_4$alkyl, for example methyl, ethyl, n- or i-propyl and n-, i- or t-butyl; and for aryl it is preferably phenyl or naphthyl. Especially preferred $R_8$ is H, Cl, CN, phenyl or $C_1$ to $C_4$ alkyl.

$R_9$ means as alkyl preferably $C_1$–$C_4$ alkyl, for example methyl, ethyl, n- or i-propyl and n-, i- or t-butyl. In the group —C(O)O—$R_{11}$, $R_{11}$ means preferably H or $C_1$–$C_{12}$alkyl, more preferably $C_1$–$C_6$ alkyl, like for example methyl, ethyl, propyl, butyl, pentyl, hexyl, heptyl, octyl, nonyl, decyl, undecyl, dodecyl, tetradecyl, hexadecyl and octadecyl. Especially preferred $R_9$ is H, —C(O)OH or —C(O)—O—$C_1$–$C_4$alkyl.

$R_{10}$ means as alkyl preferably $C_1$–$C_4$alkyl, for example methyl, ethyl, n- or i-propyl and n-, i- or t-butyl, as aryl preferably phenyl and naphthyl, and as aralkyl preferably benzyl. $R_{10}$ means preferably H, $C_1$–$C_4$alkyl, phenyl, pyrrolidonyl, F, Cl, CN or the group —$X_1$—$(R_1)_r$—$(X_2)_s$—H. $R_{11}$ may be for example H, K, Na, $C_1$–$C_6$alkyl, $C_1$–$C_6$-hydroxyalkyl, cyclohexyl, cyclopentyl, cyclohexylmethyl, phenyl, methylphenyl, benzyl or methylbenzyl.

The weight ratio of structural elements of formula IV to other structural units is dependent on the actual practical application, hence there are no well defined preferred ratios, other than the broad range 9995:5 to 5:9995. In certain applications where both color strength and fluorescence are required, then the preferred ratios of structural units IV to other structural units is 20:80 to 9995:5, preferably 50:50 to 9995:5 and more preferably 80:20 to 9995:5. In circumstances where fluorescence is desired but color strength is not required, then the preferred ratio of chromophore structural units to non-fluorescent structural units is 20:80 to 5:9995, more preferably 10:90 to 5:9995 and more preferably 5:95 to 5:9995.

The amount of guest is system dependent, hence there is no well defined ratios. In general the structural elements of formula IVa may be present in an amount of 0.05 to 50 weight %, preferably 0.1 to 5 weight %, more preferably 0.1 to 5 weight %, most preferably 0.1 to 3 weight % of the polymer.

The weight ratio of structural elements of formula V to fluorescent structural units is dependent on the actual practical application, hence there are no well defined preferred ratios, other than the broad range 0:999 to 999:1. In certain applications where both color strength and fluorescence are required, then the preferred ratios structural elements of formula V to fluorescent structural units is 20:80 to 0:100, more preferably 10:90 to 0:100 and more preferably 5:95 to 0:100. In circumstances where fluorescence is desired but color strength is not required, then the preferred ratio structural elements of formula V to fluorescent structural units is 20:80 to 999:1, preferably 50:50 to 999:1 and more preferably 80:20 to 999:1

The polymers with the structural elements of formulae IV, IVa and optionally V may be crosslinked in combination with multi-functional monomers, for example with 0.01 to 80 weight-%, preferably 0.1 to 60 weight-% of these monomers, related to 100 g of the polymer. Depending upon the kind of the polymer, at least trifunctional carboxylic acids, isocyanates, alcohols, amines, vinyls or epoxides may be used. Furthermore residues containing at least two olefinically (ethylenically) unsaturated groups may be employed. The ethylenically unsaturated crosslinking agent may be selected from the group consisting of divinylbenzol, bi-di-methylmaleinimide-alkylene like bi-(dimethylmaleinimidyle)-methylene or -ethylene, acrylic acid- or methacrylic acid esters or -amides of polyols, preferably diols to tetrols, or polyamines respectively, preferably diamines to tetramines.

Preferred ethylenically unsaturated crosslinking agents are selected from the group of acrylic or methacrylic acid esters of aliphatic, cycloaliphatic and cycloaliphatic-aliphatic diols to tetrols and diamines to tetramines containing especially preferred 2 to 12, and particularly preferred 2 to 8 C-atoms. Some examples of these diols are alkylenediols like ethylenglycol, 1,2- or 1,3-propanediol, 1,2-, 1,3- and 1,4-butanediol, pentanediol, hexanediol, octanediol, decanediol, dodecanediol, cyclohexanediol, di(hydroxymethyl)-cyclohexane, polyoxyalkylendiols from preferably $C_2$–$C_6$alkylendiols with preferably 2 to 100 alkylenediol units, more preferably 2 to 50 alkylenediol units, and most preferably 2 to 20 alkylenediol units, like for example polyethylenediols, polypolypropylenediols, polybutylenediols and polyethylene/polypropylenediols, further 1,1,1-trihydroxymethylethane or -propane, pentaerythritol and dipentaerythritol. Some examples for polyamines are ethylenediamine, 1,3- and 1,3-propanediamine, 1,2-, 1,3- and 1,4-butanediamine, 1,6-hexanediamine, diethylenetriamine, triethylenetetramine, cyclohexanediamine, (aminomethyl)cyclohexaneamine, isophorondiamine and di-(aminomethyl)cyclohexane.

In a preferred embodiment of the invention the polymers contain structural elements of the formulae VI and VIa,

(VI)

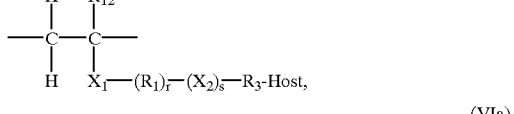

(VIa)

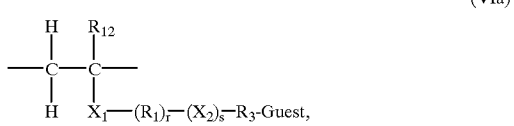

wherein $R_{12}$ is H or methyl, and $X_1$, $X_2$, $R_1$, $R_3$, Guest, Host, r and s have the same meanings as described before, including the preferred embodiments; and optionally structural elements of formula V. The group $—X_1—(R_1)_r—(X_2)_s—R_3—$ in the structural elements of formulae VI and VIa mean preferably $—C(O)—O—$, $—C(O)—O—C_2$-$C6$ alkylene-$O—C(O)—$, $—C(O)—O—(C_2$-$C_6$ alkylene-O)$_u$—C(O)—$ with u being a number from 2 to 10, $—O—C(O)—C_6H_5—CH_2—$, $—O—C(O)—C_6H_5—$ or $—O—C(O)—C_1$ to $C_{12}$ alkylene.

The polymers with the structural elements of formulae IV, IVa, or VI, VIa, and optionally V, may be additionally crosslinked with at least difunctional monomers.

The polymers with the structural elements of formulae IV and IVa or VI and Via, and optionally structural elements of formula V may contain additionally equal or different structural elements of formula VII,

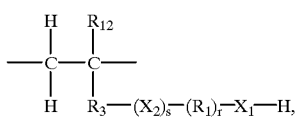

(VII)

wherein $R_{12}$, $X_1$, $X_2$, $R_1$, $R_3$, r and s have the meanings given before, inclusive of the preferred embodiments. These structural elements are especially present when the groups Host and Guest are introduced to the polymer through reaction between pendant functional groups on the polymer and functional groups on the respective host and guest molecules.

The polymers with the structural elements of formulae IV and IVa or VI and VIa, and optionally structural elements of formula V, contain preferably equal or different structural elements of formula VII as preferred units of formula V,

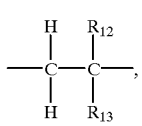

(VIII)

wherein $R_{12}$ means H or methyl, and $R_{13}$ means H, $C_1$–$C_4$alkyl, $C_1$–$C_4$alkoxy, —CN, Cl, phenyl, pyrrolidonyl, pyridinyl, imidazolyl, —C(O)O$R_{14}$ or —C(O)—N$R_{15}R_{16}$, $R_{14}$ means H or $C_1$–$C_{18}$— and preferably $C_1$–$C_{12}$alkyl, and $R_{15}$ and $R_{16}$ independently of one another mean H or $C_1$–$C_{12}$—, and preferably $C_1$–$C_6$alkyl.

The polymers with the structural elements of formulae IV and IVa, or VI and VIa, and optionally equal or different structural elements of formula V or formula VIII, may additionally contain structural elements of formulae IX or X as preferred units of crosslinking agents,

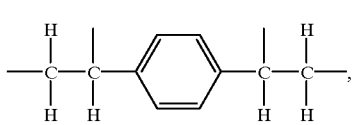

(IX)

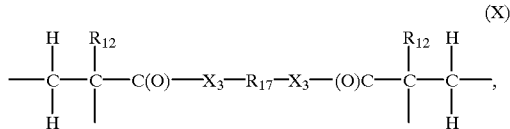

(X)

wherein $R_{12}$ means H or methyl, $X_3$ means —O—, —NH— or —N($C_1$-$C_4$-alkyl)-, and $R_{17}$ means $C_2$-$C_{12}$— and preferably $C_1$-$C_6$ alkylene, cyclohexylene, cyclohexanedimethylene, phenylene, or $X_3$ means —O— and $R_{17}$ means $C_2$-$C_6$alkylene-($C_2$-$C_6$alkylen-O)$_{2\ to\ 20}$—$C_2$-$C_6$alkylene.

The polymerisates and preferred polymerisates described before may contain additionally equal or different ionic structural elements, for example of formula XI,

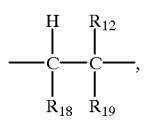

(XI)

wherein $R_{12}$ means H or methyl, $R_{18}$ means H and $R_{19}$ means —C(O)O$R_{20}$, —SO$_3$$R_{20}$, —C$_6$H$_4$—COO$R_{20}$, —C$_6$H$_4$—SO$_3$$R_{20}$, —C$_6$H$_4$—$R_{21}$ or —C(O)—$X_4$—$C_2$-$C_6$ alkylene-$R_{22}$, X4 means —O— or —NH—, $R_{18}$ and $R_{19}$ mean independently of one another —C(O)O$R_{20}$ or —C(O)—$X_4$—$C_2$-$C_6$alkylene-$R_{22}$, $R_{20}$ means an alkaline metal, preferably Li, Na or K, $R_{21}$ means an ammonium group or an ammoniummethyl group, and $R_{22}$ means an ammonium group.

The ammonium group or the ammonium in the ammoniummethyl group may be derived from primary, secondary or tertiary amine groups, preferred are quaternary ammonium groups. The ammonium groups or the ammonium in the ammoniummethyl group may correspond to the formula XII,

—$^+$N$R_{23}$$R_{24}$$R_{25}$ (XII), wherein $R_{23}$, $R_{24}$ and $R_{25}$ are independently from one another H, $C_1$-$C_{18}$—, preferably $C_1$-$C_{12}$— and more preferably $C_1$-$C_6$ alkyl, $C_5$- or $C_6$cycloalkyl, phenyl, benzyl, 1-phenyl-2-ethyl, or $R_{23}$ and $R_{24}$ together are tetramethylene, pentamethylene or —CH$_2$CH$_2$—O—CH$_2$CH$_2$—; $R_{26}$ has the meaning as given before.

Suitable counter anions may be derived from inorganic or organic acids, like for example carboxylic acids, sulfonic acids and halogenhydrogen acids. Preferred counter anions are chloride and bromide.

The polymerisates and preferred polymerisates described before may contain additionally structural elements with acidic groups like for example —C(O)OH or —SO$_3$H, especially when emulsion polymerisates are involved.

The structural elements with acidic groups may correspond to the formula XII,

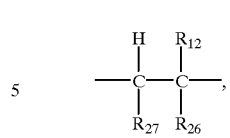

(XIII)

wherein $R_{12}$ means H or methyl, $R_{27}$ means H and $R_{26}$ means —C(O)OH, —SO$_3$H, —C$_6$H$_4$—COOH, —C$_6$H$_4$—SO$_3$H, or $R_{26}$ and $R_{27}$ means —C(O)OH.

Polymers with amino or acidic groups may be preferably soluble in water or they may be prepared by emulsion polymerization for dispersing and/or dissolving monomers.

In another preferred embodiment the polymers according to the invention may be crosslinked with difunctional host and/or guest molecules. These polymers may contain recurring structural elements of formulae XIV, XIVa or both, alone or together with structural elements of formula IV, IVa or both,

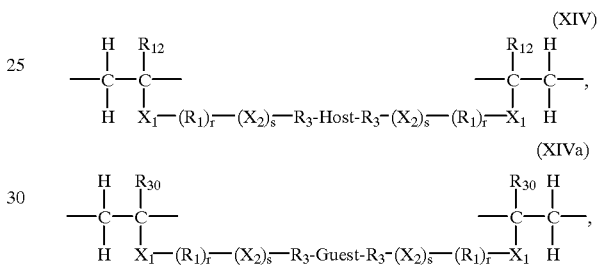

wherein $R_1$, $R_3$, $R_{12}$, $X_1$, $X_2$, r, s, -Host- and -Guest- have the meanings given before, inclusive of preferred embodiments.

The weight ratio of structural elements of formula XIV to other structural units is dependent on the actual practical application, hence there are no well defined preferred ratios, other than the broad range 9995:5 to 5:9995. In certain applications where both color strength and fluorescence are required, then the preferred ratios of structural units XIV to other structural units is 20:80 to 9995:5, preferably 50:50 to 9995:5 and more preferably 80:20 to 9995:5. In circumstances where fluorescence is desired but color strength is not required, then the preferred ratio of chromophore structural units to non-fluorescent structural units is 20:80 to 5:9995, more preferably 10:90 to 5:9995 and more preferably 5:95 to 5:9995.

The amount of guest is system dependent, hence there is no well defined ratios. In general the structural elements of formula XIVa may be present in an amount of 0.05 to 50 weight %, preferably 0.1 to 5 weight %, more preferably 0.1 to 5 weight %, most preferably 0.1 to 3 weight % of the polymer.

The above crosslinked polymers with one or both structural elements of formulae XIV and XIVa may contain structural elements of formulae IV, IVa, V, VII, IX, X, XI, XII and XIII alone or in any combination of at least 2 of these structural elements, or may contain structural elements of preferred residues formulae V, IX and VII, and further IX, X, XI, XII and XIII alone or in any combination of at least 2 of these structural elements.

Some preferred examples of structural units of formula XIVa are

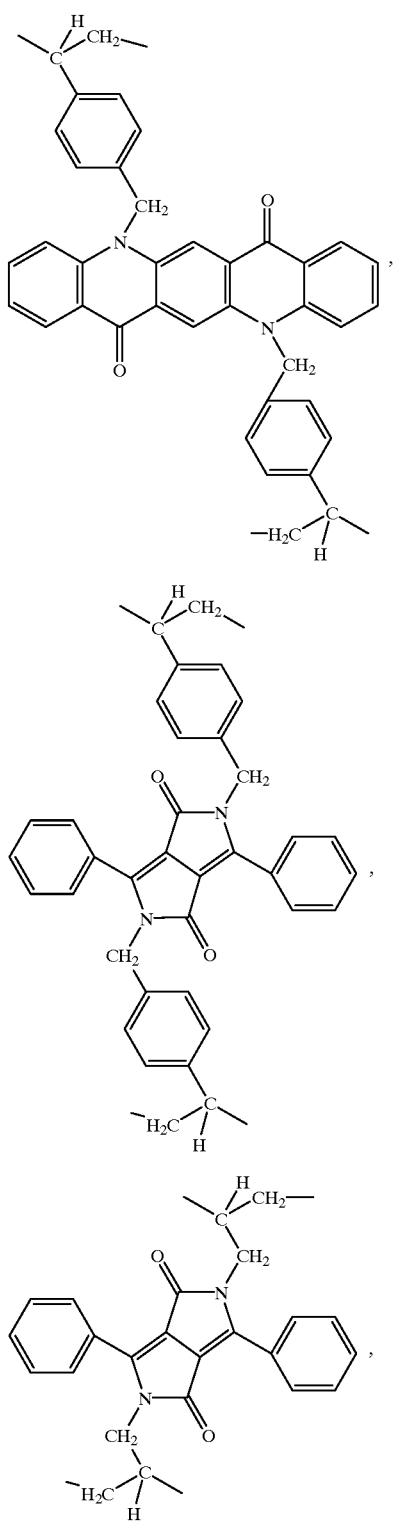

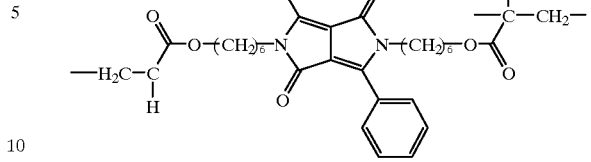

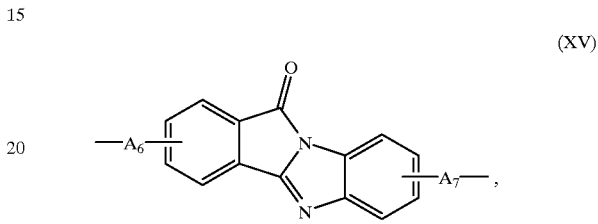

Preferred divalent residues of the host chromophore correspond to the formula XV, $$\text{(XV)}$$

wherein neighboring carbon atoms of the benzene rings can be condensed with benzene rings, heteroaromatic rings or both, and to these rings can be linked free bonds rather than to the benzene rings of the polycyclic core structure, and the aromatic rings are unsubstituted or substituted with halogens like F, Cl or Br, —CN, —$NO_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, C, to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{18}$ aralkylthio, $C_5$ to $C_{17}$ heteroaralkylthio, $C_1$ to $C_{18}$ alkyl-SO— or —$SO_2$, $C_3$ to $C_{12}$ cycloalkyl-SO— or —$SO_2$, $C_6$ to $C_{18}$ aryl-SO— or —$SO_2$, $C_5$ to $C_{17}$ heteroaryl-SO— or —$SO_2$, $C_3$ to $C_{12}$ cycloalkylalkyl-SO— or —$SO_2$, $C_6$ to $C_{18}$ aralkyl-SO— or —$SO_2$, $C_5$ to $C_{17}$ heteroaralkyl-SO— or —$SO_2$, secondary amino with 2 to 30 carbon atoms, and alkoxyalkyl with 2 to 20 carbon atoms, the cyclic aliphatic and aromatic residues (substituents) may also be substituted, for example with halogens like F, Cl or Br; or —CN, —$NO_2$, $C_1$ to $C_{18}$ alkyl, $C_3$ to $C_{12}$ cycloalkyl, $C_6$ to $C_{18}$ aryl, $C_3$ to $C_{12}$ cycloalkylalk, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, and $A_6$ and $A_7$ mean a direct bond or a divalent organic group.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-$SO_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 or 2 rings are condensed with the neighboring carbon atoms to bicyclic or tricyclic systems. They may be selected from benzene, furane, thiophene, pyrrole, pyridine, and pyrimidine.

In a preferred embodiment, $A_6$ and $A_7$ correspond to the formula XVI,

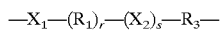 (XVI), wherein $X_1$, $X_2$, $R_1$, $R_3$, r and s have the meanings described before, inclusive of the preferred embodiments.

In a preferred embodiment the bivalent host residues correspond to formulae XVII and XVIIa,

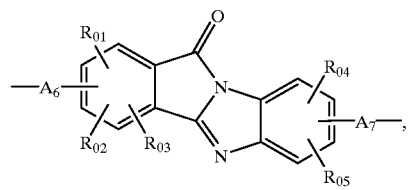 (XVII)

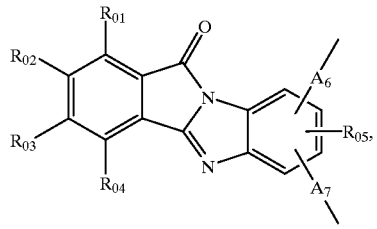 (XVIIa)

wherein $R_{01}$, $R_{02}$, $R_{03}$, $R_{04}$, and $R_{05}$ independently from one another mean H, Cl, $C_1$ to $C_{18}$ alkyl, $C_1$ to $C_{18}$ alkoxy, phenyl, benzyl, $C_1$ to $C_{12}$ alkylphenyl or $C_1$ to $C_{12}$ alkylbenzyl. $R_{05}$ preferably means H, and $A_6$ and $A_7$ correspond to a bivalent residue of formula XVI.

In a preferred embodiment the groups $A_6$ and $A_7$ may be selected from the formulae

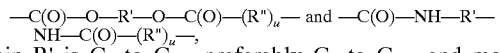

wherein R' is $C_2$ to $C_{20}$, preferably $C_2$ to $C_{12}$, and more preferably $C_2$ to $C_6$alkylene, phenylene, benzylene, or oligoxyalkylene with preferably 2 to 6, and more preferably 2 to 4 oxyethylene and/or oxypropylene units, R" means $C_1$ to $C_{12}$alkylene, phenylene or benzylene, and u means 0 or 1.

Some preferred examples of host chromophore residues corresponding to formula XIV are

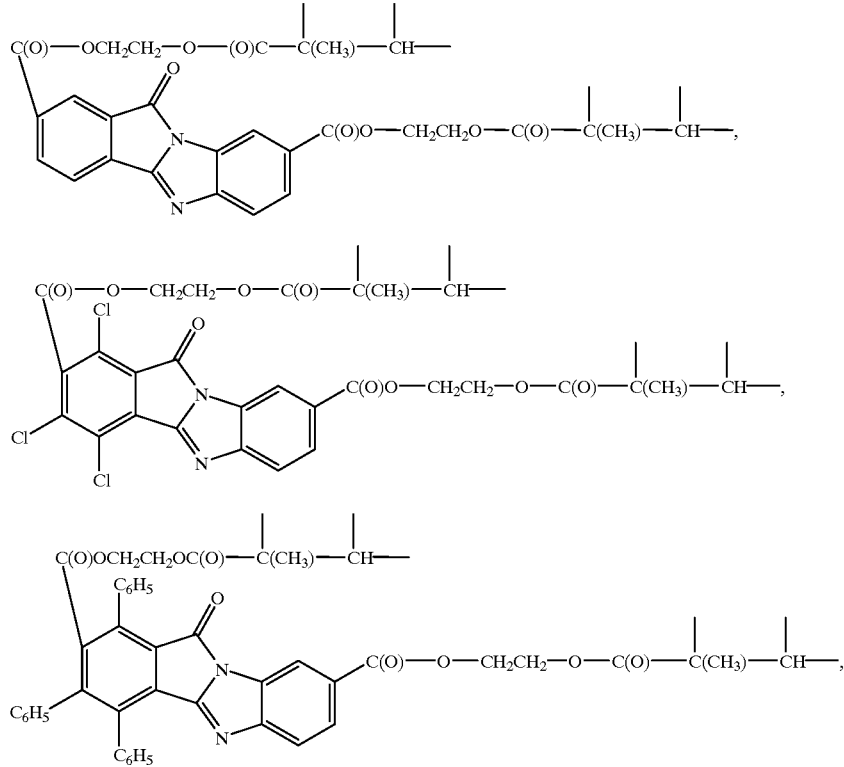

-continued

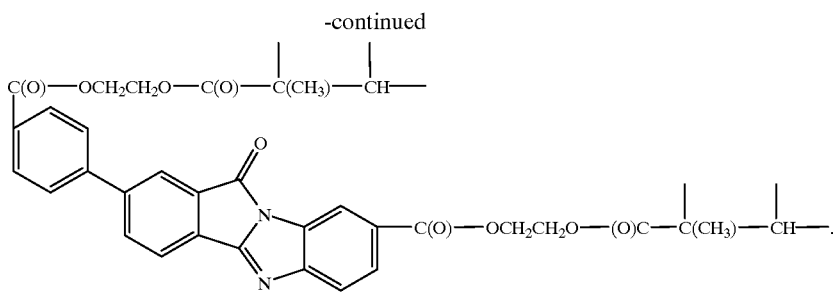

In another preferred embodiment of the invention, the polymer according to the invention may contain functional host monomers which themselves possess two or three functional groups covalently linked via a bridging group to one ring of the host core structure. Thus the polymers with recurring structural units of the formulae III, IIIa, IIIb and IIIc may additionally contain, or in the case of IIIb all units, be replaced by recurring crosslinking units of the formula IIIe, IIIf or both,

wherein
$A_8$ means a trivalent or tetravalent organic residue, copolymerisable with the groups A to $A_4$, and
Host is a monovalent fluorescent host chromophore, as defined before.

Preferred divalent and trivalent residues of the host chromophore may also correspond to the formulae XXV and XXVa,

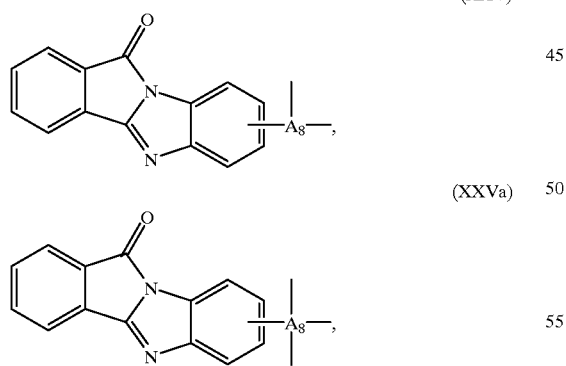

wherein
neighboring carbon atoms of the benzene ring can be condensed with benzene rings, heteroaromatic rings or both, and
the aromatic rings are unsubstituted or substituted with halogens like F, Cl or Br, —CN, —NO$_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{12}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO— or —SO$_2$, $C_3$ to $C_{12}$ cycloalkyl-SO— or —SO$_2$, $C_6$ to $C_{18}$ aryl-SO— or —SO$_2$, $C_5$ to $C_{17}$ heteroaryl-SO— or —SO$_2$, $C_3$ to $C_{12}$ cycloalkylalkyl-SO— or —SO$_2$, $C_6$ to $C_{18}$ aralkyl-SO— or —SO$_2$, $C_5$ to $C_{17}$ heteroaralkyl-SO— or —SO$_2$, secundary amino with 2 to 30 carbon atoms, and alkoxyalkyl with 2 to 20 carbon atoms, the cyclic aliphatic and aromatic residues (substituents) may also be substituted, for example with halogens like F, Cl or Br; or —CN, —NO$_2$, $C_1$ to $C_{18}$ alkyl, $C_3$ to $C_{12}$cycloalkyl, $C_6$ to $C_{18}$ aryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, and $A_8$ mean a trivalent or tetravalent organic group.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 ring is condensed with the neighboring carbon atoms to form bicyclic systems. They may be selected from benzene, furane, thiophene, pyrrole, pyridine, and pyrimidine.

In a preferred embodiment, AB corresponds to the formulae XXVI or XXVIa,

wherein
(a) $R_{31}$ is a direct bond, $C_1$ to $C_{12}$ alkylene, phenylene or benzylene;
$X_4$ is N, O, S, C(O)O or C(O)N;
$R_{32}$ means $C_2$ to $C_{12}$ alkyltriyl, phenyltriyl or benztriyl, when a is 1 and b is 2, or means $C_2$ to $C_{12}$ alkyltetrayl, phenyltetrayl or benztetrayl, when a is 1 and b is 3;
$X_5$ means O, S, NH, C(O)O, C(O)NH,

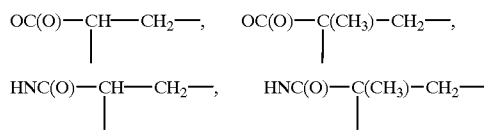

or (b) $R_{32}$ is a bond, a is 0 and b is 2 or 3, $X_5$ has the above meanings and $R_{31}$ means $C_2$ to $C_{12}$ alkyltriyl, phenyltriyl or benztriyl, when b is 2, or means $C_2$ to $C_{12}$ alkyltetrayl, phenyltetrayl or benztetrayl, when b is 3;

(c) $R_{31}$ is a direct bond, $C_1$ to $C_{12}$ alkylene, phenylene or benzylene;

$X_6$ is N or C(O)N;

$R_{33}$ is $C_2$ to $C_{12}$ alkylene;

$X_7$ is O, S, C(O)O, C(O)NH, and

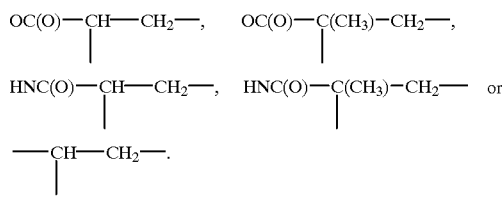

$R_{31}$ and $R_{33}$ in the meaning of alkylene preferably contains 2 to 8 and more preferably 2 to 4 C-atoms. $R_{32}$ in the meaning of alktriyl contains preferably 2 to 8, more preferred 2 to 6, and most preferred 2 to 4 C-atoms.

In a preferred embodiment the bivalent host residues correspond to formulae XXVII and XXVIIa, (XXVII)

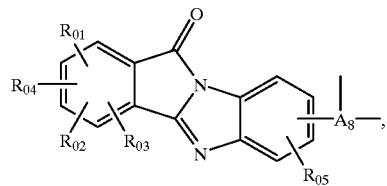

(XXVII)

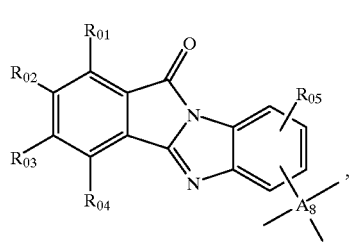

wherein $R_{01}$, $R_{02}$, $R_{03}$, $R_{04}$, and $R_{05}$ independent from one another mean H, Cl, $C_1$ to $C_{18}$ alkyl, $C_1$ to $C_{18}$ alkoxy, phenyl, benzyl, $C_1$ to $C_{12}$ alkylphenyl or $C_1$ to $C_{12}$ alkylbenzyl, and $A_8$ corresponds to formulae XXVI or XXVIa. $R_{05}$ means preferably H.

In a preferred embodiment the group $A_8$ may be selected from;

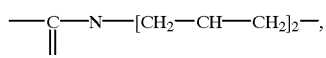
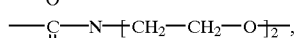
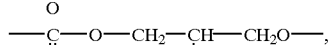
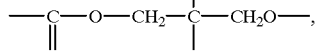
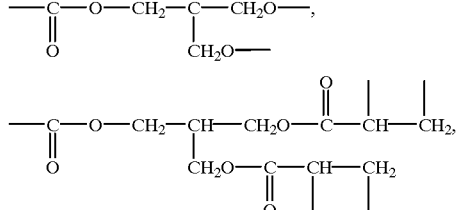
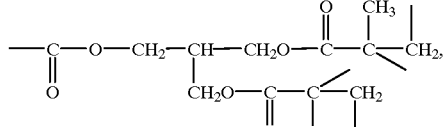
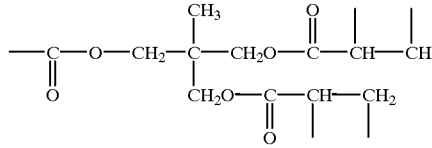
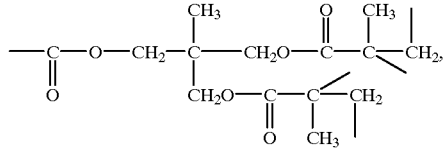
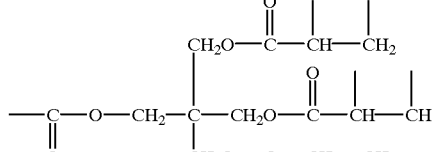
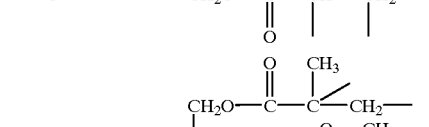
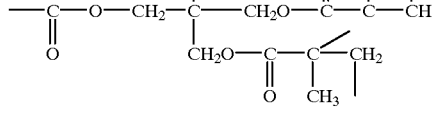

Some preferred examples are residues from the group (Ph means phenyl):

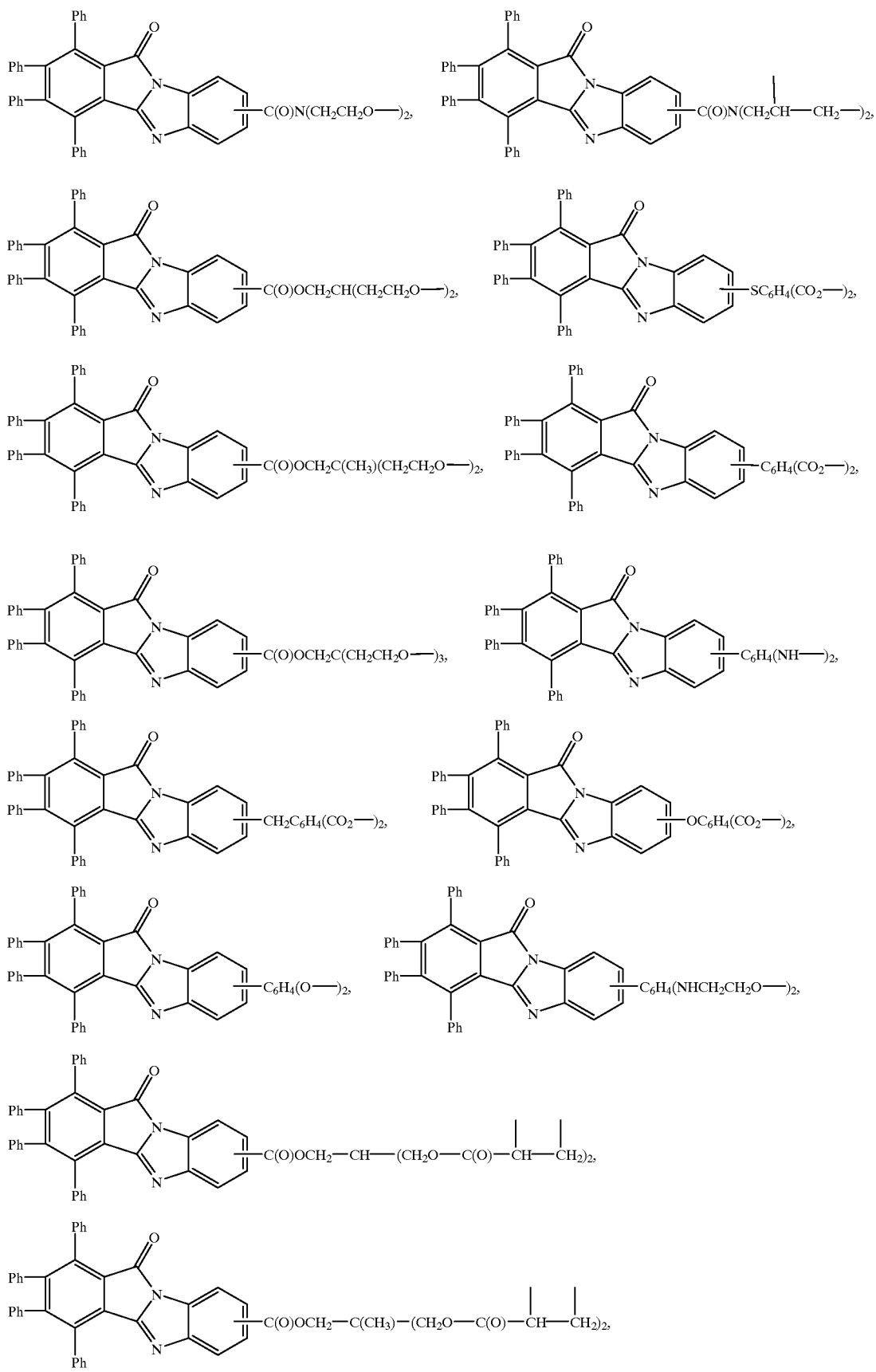

-continued

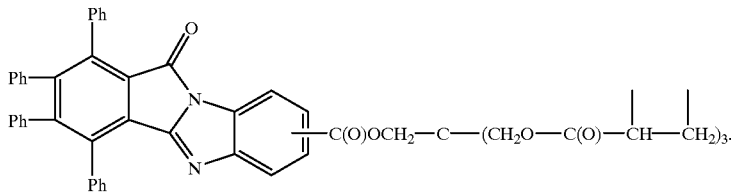

The polymers according to the invention may be random, block, graft or emulsion polymers (latices).

The preparation of polymers and their immobilization is well known in the art. One such method is to polymerize monomers with pendent host and guest molecules, whilst another is to use polymers with pendent functional groups and to react them with host and guest molecules that also possess functional groups.

A further preferred embodiment of the invention is a process for the manufacture of the polymers according to the invention, which involves reacting a compound of the formula XVIII, XIX, XX, XXI and XXVIII in any host/guest combination, alone or together with comonomers,

| | |
|---|---|
| $A'_1$-Guest | (XVIII), |
| $A'_2$-Host | (XIX), |
| $A'^3$-Host-$A'_3$ | (XX), |
| $A'^4$-Guest-$A'_4$ | (XXI), |
| Host-$(A'_5)_c$ | (XXVIII), | wherein $A'_1$ is a monovalent functional or polymerizable group, $A'_2$ is a monovalent functional or polymerizable group coreactive with $A'_1$, $A'_3$ is a monovalent functional or polymerizable group coreactive with $A'_1$ and $A'_2$, $A_4$ is a monovalent functional or polymerisable group coreactive with $A'_1$, $A'_2$ and $A'_3$, $A'_5$ is monovalent functional or polymerizable group, coreactive with $A'_1$, $A'_2$, $A'_3$ and $A_4$, and c is 2 or 3, and Guest and Host have the meanings as given before, whereby the $A'_1$, $A_2$, $A'_3$ and $A_4$ are linked directly or via a bridging group to the host and guest core structures.

A further preferred embodiment of the invention is a process for the manufacture of polymers according to completion form (A), which involves the reaction of a polymer having recurring structural elements each containing, either directly or through a bridging group, covalently linked functional or polymerisable groups, with a compound of the formula XVIII, XIX, XX and XXI in any host/guest combination, alone or together with comonomers,

| | |
|---|---|
| $A'_1$-Guest | (XVIII), |
| $A'_2$-Host | (XIX), |
| $A'^3$-Host-$A'_3$ | (XX), |
| $A'^4$-Guest-$A'_4$ | (XXI), |
| Host-$(A'_5)_c$ | (XXIIX), | wherein $A'_1$ is a monovalent functional or polymerisable group, $A'_2$ is a monovalent functional or polymerisable group coreactive with functional or polymerisable groups on the polymer, $A'_3$ is a monovalent functional or polymerisable group coreactive with functional or polymerisable groups on the polymer, $A'_4$ is a monovalent functional or polymerisable group coreactive with functional or polymerisable groups on the polymer, $A'5$ is a monovalent functional or polymerisable group coreactive with functional or polymerisable groups on the polymer and c is 2 or 3, and Guest and Host have the meanings given before, whereby the $A'_1$, $A_2$, $A'_3$, $A_4$ and $A'_5$ are linked directly or via a bridging group to the host and guest core structures.

The preparation of the polymers according to the invention may be carried out according to processes well known in the art of polymer chemistry such as step growth, anionic, cationic and radical polymerisations. Polymerization processes for example are solution, bulk, emulsion, photo- and interface polymerization.

Reaction temperatures in general may range from 0 to 250° C. The use of suitable and well established catalysts and photoinitiators are not described in detail herein. Azo-bisisobutyronitrile is well known as an effective radical catalyst for thermal polymerisations of olefinically unsaturated compounds. The polymerization may be carried out by mixing the monomers, catalysts and optionally a solvent together and heating, irradiating or by both heating and irradiating. The polymers may be isolated by precipitation into non-solvents or removing the solvents. If required further purification can be performed by means of repeat precipitations and drying.

The monomers are partially novel and partially known or they can be prepared by known or analogous methods.

Functional guest chromophores are known or can be synthesized by known or analogous methods for their synthesis by employing optionally protected functional intermediates. Guest chromophores may be obtained from chromophore precursors containing NH-groups by the reaction with halogenalkanes which additionally contain a functional group such as a carboxylic group or a vinyl group.

Multi-functional guest compounds can be prepared in a similar fashion to those described in the literature EP 0 337 951.

The host monomers can be prepared according to the methods described in EP 0 456 609 wherein phthalic anhydride is reacted with 1,2-diaminobenzenes, such that the anhydride, the diaminobenzenes or both contain optionally protected functional groups.

Difunctional benzo[4,5]imidazo[2,1-a]isoindol-11-ones are novel, and in one aspect a further preferred embodiment of the invention are compounds of formula XXII,

| | |
|---|---|
| $A''_1$-Host-$A''_1$ | (XXII), | wherein $A''_1$ is a monovalent functional (also means polymerisable) group, which is linked directly or via a bridging group to the host body, and host is a divalent benzo[4,5]imidazo[2,1-a]isoindol-11-one, neighboring carbon atoms of the benzene rings of the host can be condensed with benzene rings, heteroaromatic rings or both, and to these rings can be linked the functional group rather than to the benzene rings of the host core structure, and the aromatic rings are unsubstituted or substituted with F, Cl or Br, —CN, —NO$_2$, C$_1$ to C$_{18}$ alkyl, C$_3$ to C$_{12}$ cycloalkyl, C$_6$ to C$_{18}$ aryl, C$_5$ to C$_{17}$ heteroaryl, C$_3$ to C$_{12}$ cycloalkylalkyl, C$_6$ to C$_{18}$ aralkyl, C$_5$ to C$_{17}$heteroaralkyl, C$_1$ to C$_{18}$alkyloxy, C$_3$ to C$_{12}$ cycloalkyloxy, C$_6$ to C$_{18}$aryloxy, C$_5$ to C$_{17}$heteroaryloxy, C$_3$ to C$_{12}$cycloalkylalkyloxy, C$_6$ to C$_{18}$aralkyloxy, C$_5$ to C$_{17}$heteroaralkyloxy, C$_1$ to C$_{18}$alkylthio, C$_3$ to C$_{12}$cycloalkylthio, C$_6$ to C$_{18}$arylthio, C$_5$ to C$_{17}$heteroarylthio, C$_3$ to C$_{12}$cycloalkylalkylthio, C$_6$ to C$_{18}$aralkylthio, C$_5$ to C$_{17}$heteroaralkylthio, C$_1$ to C$_{18}$alkyl-SO— or —SO$_2$, C$_3$ to C$_{12}$cycloalkyl-SO— or —SO$_2$, C$_6$ to C$_{18}$aryl-SO— or —SO$_2$, C$_5$ to C$_{17}$heteroaryl-SO— or —SO$_2$, C$_3$ to C$_{12}$cycloalkylalkyl-SO— or —SO$_2$, C$_6$ to C$_{18}$aralkyl-SO— or —SO$_2$, C$_5$ to C$_{17}$heteroaralkyl-SO— or —SO$_2$, secandary amino with 2 to 30 carbon atoms, and alkoxyalkyl with 2 to 20 carbon atoms, with the proviso that additionally at least one of the substituents is linked to a benzene ring, when two —NH$_2$ groups, seperately, are bonded directly to different benzene rings; and two OH groups are directly bonded to one benzene ring.

The cyclic aliphatic and aromatic residues may be also substituted, with for example F, Cl or Br, —CN, —NO$_2$, C$_1$ to C$_{18}$alkyl, C$_3$ to C$_{12}$cycloalkyl, C$_6$ to C$_{18}$aryl, C$_3$ to C$_{12}$cycloalkyalkyl, C$_6$ to C$_{18}$aralkyl, C$_5$ to C$_{17}$heteroaralkyl, C$_1$ to C$_{18}$alkyloxy, C$_3$ to C$_{12}$cycloalkyloxy, C$_6$ to C$_{18}$aryloxy.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 or 2 rings are condensed with the neighboring carbon atoms to form bicyclic or tricyclic systems. They may be selected from the group consisting of benzene, furane, thiophene, pyrrole, pyridine, and pyrimidine.

In a preferred embodiment, the bridging group corresponds to the formula XXIII,

                                      (XXIII), wherein

X$_1$, X$_2$, R$_1$, R$_3$, r and s have the meanings as given before, inclusive of the preferred embodiments.

The functional groups A"$_1$ may be selected from the group consisting of alkyl bonded halogen like Cl and Br; —N$_3$, epoxide, —OH, —SH, —CN, —NHR$_{100}$, =C=NR$_{100}$, =CO, —CH—O, —NCO, —CH=CH$_2$, —C(CH$_3$)=CH$_2$, —C(O)OH, —SO$_3$H, —SO$_2$Cl, —SO$_2$Br, —C(O)—Cl, —C(O)—Br, —OC(O)—OR$_{101}$, —OC(O)—NR$_{102}$R$_{103}$, —C(O)—OR$_{104}$, —SO$_2$—OR$_{104}$, —C(O)—NR$_{102}$R$_{103}$, and —SO$_2$—NR$_{102}$R$_{103}$, wherein R$_{100}$ means H, C$_1$–C$_{18}$alkyl, phenyl, or benzyl,
R$_{101}$ means C$_1$–C$_{18}$alkyl, phenyl, or benzyl,
R$_{102}$ and R$_{103}$ independently from one another mean H, C$_1$–C$_{18}$alkyl, phenyl, or benzyl, and
R$_{104}$ means C$_1$–C$_{18}$alkyl, phenyl, or benzyl.

R$_{100}$, R$_{101}$, R$_{102}$, R$_{103}$ and R$_{104}$ contain as alkyl preferably 1 to 12, more preferably 1 to 8 and most preferably 1 to 4 carbon atoms.

More preferred functional groups A"$_1$ are selected from the group consisting of alkyl linked Cl and Br; epoxide, —OH, —SH, —NHR$_{100}$, —CH=CH$_2$, —C(CH$_3$)=CH$_2$, —NCO, —C(O)OH, —C(O)—Cl, —C(O)—Br, —C(O)—OR$_{104}$, —C(O)—NR$_{102}$R$_{103}$, wherein R$_{100}$ means H or C$_1$–C$_{12}$alkyl,
R$_{102}$ and R$_{103}$ independently from one another means H or C$_1$–C$_4$alkyl, and
R$_{104}$ means C$_1$–C$_8$alkyl.

In a mostly preferred embodiment the compounds correspond to formulae XXIV and XXIVa,

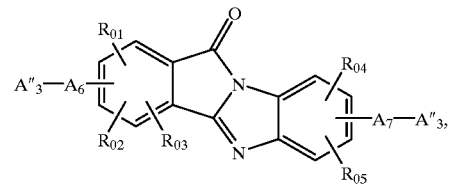

(XXIV)

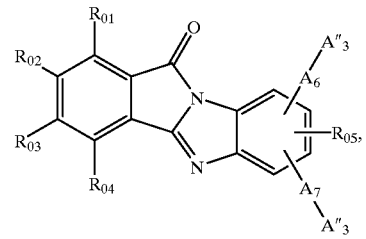

(XXIVa)

wherein

R$_{01}$, R$_{02}$, R$_{03}$, R$_{04}$, and R$_{05}$ independently from one another mean H, Cl, C$_1$ to C$_{18}$alkyl, C$_1$ to C$_{18}$alkoxy, phenyl, benzyl, C$_1$ to C$_{12}$ alkylphenyl or C$_1$ to C$_{12}$alkylbenzyl, A$_6$ and A$_7$ correspond to a bivalent residue of formula XXXIII, and A"3 is selected from the group consisting of alkyl linked Cl and Br; epoxide, —OH, —SH, —NHR$_{100}$, —CH=CH$_2$, —C(CH$_3$)=CH$_2$, —NCO, —C(O)OH, —C(O)—Cl, —C(O)—Br, —C(O)—OR$_{104}$, —C(O)—NR$_{102}$R$_{103}$, wherein R$_{100}$ means H or C$_1$–C$_{12}$alkyl,
R$_{102}$ and R$_{103}$ independently from one another mean H or C$_1$–C$_4$alkyl, and
R$_{104}$ means C$_1$–C$_8$alkyl. R$_{05}$ means preferably H.

In an especially preferred embodiment the bivalent groups A$_6$ and A$_7$ may be selected from the formulae

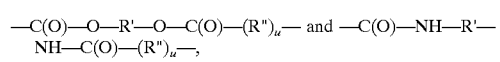

wherein R' is C$_2$ to C$_{20}$, preferably C$_2$ to C$_{12}$, and more preferably C$_2$ to C$_6$alkylene, phenylene, benzylene, or oligoxyalkylene with preferably 2 to 6, and more preferably 2 to 4 oxyethylene and/or oxypropylene units, R" means C$_1$ to C$_{12}$alkylene, phenylene or benzylene, and u means 0 or 1, and groups —CH=CH$_2$ or —C(CH$_3$)=CH$_2$ are linked to the C(O)—groups.

Especially preferred compounds correspond to the formula XXIX,

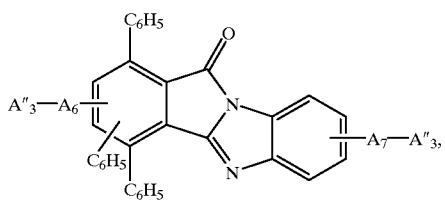

(XXIX)

wherein $A_6$ is $C_6H_4$ and $A_7$ is a direct bond or $C_1$ to $C_6$ alkylene, phenylene or benzylene, and $A''_3$ means —COOH, —C(O)—Cl, —C(O)—Br, —C(O)—OR$_{104}$, —C(O)—NR$_{102}$R$_{103}$, —C(O)O—C$_2$ to C$_{12}$ alkylene-OH, —C(O)O—C$_2$ to C$_{12}$ alkylene-O—C(O)—CH=CH$_2$, or —C(O)O—C$_2$ to C$_{12}$ alkylene-O—C(O)—C(CH$_3$)=CH$_2$.

Monofunctional benzo[4,5]imidazo[2,1-a]isoindol-11-ones except amino, hydroxyl and carboxylphenyl substituted ones, and benzo[4,5]imidazo[2,1-a]isoindol-11-ones with one polyfunctional substituent are also novel, and in one aspect a further preferred embodiment of the invention are compounds of formulae XXX and XXXa, Host-A''$_4$             (XXX), Host-A''$_5$             (XXXa), wherein A''$_4$ is a monovalent functional (also means polymerisable) group, which is linked directly or via a bridging group to the host core structure, A''$_5$ is a di- or trifunctional (also means polymerisable) group, which is linked directly or via a bridging group to the host core structure, and host is a monovalent benzo[4,5]imidazo[2,1-a]isoindol-11-one, neighboring carbon atoms of the benzene rings of the host can be condensed with benzene rings, heteroaromatic rings or both, and to these rings can be linked the functional group rather than to the benzene rings of the host core structure, and the aromatic rings are unsubstituted or substituted with F, Cl or Br, —CN, —NO$_2$, C$_1$ to C$_{18}$ alkyl, C$_3$ to C$_{12}$ cycloalkyl, C$_6$ to C$_{18}$ aryl, CS to C$_{17}$ heteroaryl, C$_3$ to C$_{12}$ cycloalkylalkyl, C$_6$ to C$_{18}$ aralkyl, C$_5$ to C$_{17}$heteroaralkyl, C$_1$ to C$_{18}$alkyloxy, C$_3$ to C$_{12}$ cycloalkyloxy, C$_6$ to C$_{18}$aryloxy, C$_5$ to C$_{17}$heteroaryloxy, C$_3$ to C$_{12}$cycloalkylalkyloxy, C$_6$ to C$_{18}$aralkyloxy, C$_5$ to C$_{17}$heteroaralkyloxy, C$_1$ to C$_{18}$alkylthio, C$_3$ to C$_{12}$cycloalkylthio, C$_6$ to C$_{18}$arylthio, C$_5$ to C$_{17}$heteroarylthio, C$_3$ to C$_{12}$cycloalkylalkylthio, C$_6$ to C$_{18}$aralkylthio, C$_5$ to C$_{17}$heteroaralkylthio, C$_1$ to C$_{18}$alkyl-SO— or —SO$_2$, C$_3$ to C$_{12}$cycloalkyl-SO— or —SO$_2$, C$_6$ to C$_{18}$aryl-SO— or —SO$_2$, C$_5$ to C$_{17}$heteroaryl-SO— or —SO$_2$, C$_3$ to C$_{12}$cycloalkylalkyl-SO— or —SO$_2$, C$_6$ to C$_{18}$aralkyl-SO— or —SO$_2$, C$_5$ to C$_{17}$heteroaralkyl-SO— or —SO$_2$, secundary amino with 2 to 30 carbon atoms, and alkoxyalkyl with 2 to 20 carbon atoms, with the proviso, that in compounds of formula XXX additionally at least one of the substituents is linked to a benzene ring, when (a1) the group OH is linked directly to a benzene ring, or (a2) when the group —NH$_2$ is bonded directly or via phenylene bridging group, or (a3) when the group COOH is bond via a phenylene bridging group to the benzene rings of the benzo[4,5]imidazo[2,1-a]isoindol-11-one core structure.

The cyclic aliphatic and aromatic residues (substituents) may be also substituted, with for example F, Cl or Br, —CN, —NO$_2$, C$_1$ to C$_{18}$alkyl, C$_3$ to C$_{12}$cycloalkyl, C$_6$ to C$_{18}$aryl, C$_3$ to C$_{12}$cycloalkylalkyl, C$_6$ to C$_{18}$aralkyl, C$_5$ to C$_{17}$heteroaralkyl, C$_1$ to C$_{18}$alkyloxy, C$_3$ to C$_{12}$cycloalkyloxy, C$_6$ to C$_{18}$aryloxy.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-SO$_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably 1 or 2 rings are condensed with the neighboring carbon atoms to form bicyclic or tricyclic systems. They may be selected from the group consisting of benzene, furane, thiophene, pyrrole, pyridine, and pyrimidine.

In a preferred embodiment, the bridging group in compounds of formula XXX corresponds to the formula XXIII, $$-X_1-(R_1)_r-(X_2)_s-R_3- \quad (XXIII),$$

wherein $X_1$, $X_2$, $R_1$, $R_3$, r and s have the meanings given before, inclusive of the preferred embodiments.

The functional groups A''$_4$ and A''$_5$ may be selected from the group consisting of halogens like Cl and Br; —N$_3$, epoxide, —OH, —SH, —CN, —NHR$_{100}$, =C=NR$_{100}$, =CO, —CH=O, —NCO, —CH=CH$_2$, —C(CH$_3$)=CH$_2$, —C(O)OH, —SO$_3$H, —SO$_2$Cl, —SO$_2$Br, —C(O)—Cl, —C(O)—Br, —OC(O)—OR$_{101}$, —OC(O)—NR$_{102}$R$_{103}$, —C(O)—OR$_{104}$, —SO$_2$—OR$_{104}$, —C(O)—NR$_{102}$R$_{103}$, and —SO$_2$—NR$_{102}$R$_{103}$, wherein R$_{100}$ means H, C$_1$–C$_{18}$alkyl, phenyl, or benzyl, R$_{101}$ means C$_1$–C$_{18}$alkyl, phenyl, or benzyl, R$_{102}$ and R$_{103}$ independently from one another means H, C$_1$–C$_{18}$alkyl, phenyl, or benzyl, and R$_{104}$ means C$_1$–C$_{18}$alkyl, phenyl, or benzyl.

R$_{100}$, R$_{101}$, R$_{102}$, R$_{103}$ and R$_{104}$ contain as alkyl preferably 1 to 12, more preferably 1 to 8 and most preferably 1 to 4 carbon atoms.

More preferred functional groups A''$_4$ and A''$_5$ are selected from the group consisting of alkyl linked Cl and Br; epoxide, —OH, —SH, —NHR$_{100}$, —CH=CH$_2$, —C(CH$_3$)=CH$_2$, —NCO, —C(O)OH, —C(O)—Cl, —C(O)—Br, —C(O)—OR$_{104}$, —C(O)—NR$_{102}$R$_{103}$, wherein R$_{100}$ means H or C$_1$–C$_{12}$alkyl, R$_{102}$ and R$_{103}$ independently from one another means H or C$_1$–C$_4$alkyl, and R$_{104}$ means C$_1$–C$_8$alkyl.

In a mostly preferred embodiment the compounds of formula XXX correspond to formulae XXXI and XXXIa,

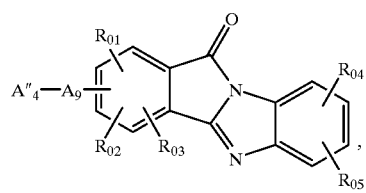

(XXXI)

-continued

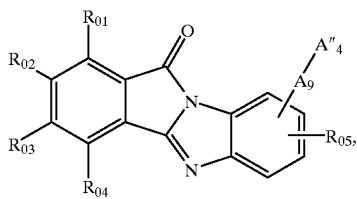
(XXXIa)

wherein $R_{01}$, $R_{02}$, $R_{03}$, $R_{04}$, and $R_{05}$ independently from one another mean H, Cl, $C_1$ to $C_{18}$alkyl, $C_1$ to $C_{18}$alkoxy, phenyl, benzyl, $C_1$ to $C_{12}$ alkylphenyl or $C_1$ to $C_{12}$alkylbenzyl, $A_g$ is a direct bond or correspond to a bivalent residue of formula XXXIII, and $A''_4$ is selected from the group consisting of alkyl linked Cl and Br; epoxide, —OH, —SH, —$NHR_{100}$, —CH=$CH_2$, —C($CH_3$)=$CH_2$, —NCO, —C(O)OH, —C(O)—Cl, —C(O)—Br, —C(O)—$OR_{104}$, —C(O)—$NR_{102}R_{103}$, wherein $R_{100}$ means H or $C_1$–$C_{12}$alkyl, $R_{102}$ and $R_{103}$ independently from one another means H or $C_1$–$C_4$alkyl, and $R_{104}$ means $C_1$–$C_8$alkyl. $R_{05}$ means preferably H.

In an especially preferred embodiment the bivalent group Ag is a direct bond, $C_1$ to $C_{12}$ alkylene, phenylene, benzylene, $C_1$ to $C_{12}$ oxyalkylene, oxyphenylene, oxybenzylene, $C_1$ to $C_{12}$ thioalkylene, thiophenylene, thiobenzylene, or the bivalent group may be selected from the formulae

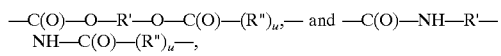

wherein R' is $C_2$ to $C_{20}$, preferably $C_2$ to $C_{12}$, and more preferably $C_2$ to $C_6$alkylene, phenylene, benzylene, or oligoxyalkylene with preferably 2 to 6, and more preferably 2 to 4 oxyethylene and/or oxypropylene units, R" means $C_1$ to $C_{12}$alkylene, phenylene or benzylene, and u means 0 or 1, and groups —CH=$CH_2$ or —C($CH_3$)=$CH_2$ are linked to the C(O)—groups.

Especially preferred compounds correspond to the formula XXXII are

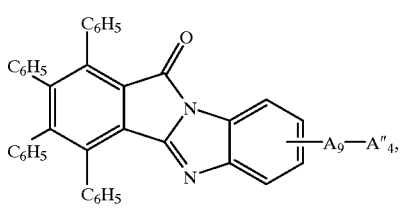
(XXXII)

wherein $A_9$ is a direct bond or $C_1$ to $C_6$ alkylene, phenylene or benzylene, and $A''_4$ means —COOH, —C(O)—Cl, —C(O)—Br, —C(O)—$OR_{104}$, —C(O)— $NR_{102}R_{103}$, —C(O)O—$C_2$ to $C_{12}$ alkylene-OH, —C(O)O— $C_2$ to $C_{12}$ alkylene-O—C(O)—CH=$CH_2$, or —C(O)O—$C_2$ to $C_{12}$ alkylene-O—C(O)—C($CH_3$)=$CH_2$.

Examples of compounds of formula XXX are (Ph means phenyl):

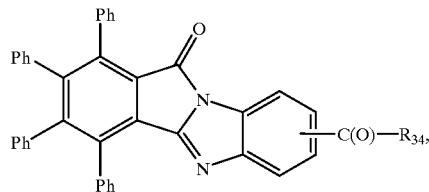

wherein $R_{34}$ is Cl, OH, $OR_{104}$ and $R_{104}$ means $C_1$–$C_8$alkyl, $NR_{102}R_{103}$ and $R_{102}$ and $R_{103}$ independently from one another mean H, $C_1$–$C_4$alkyl or $C_2$ to $C_4$ hydroxyalkyl, —C(O)O—$C_2$ to $C_{12}$ alkylene-O—C(O)—CH=$CH_2$, —C(O)O—$C_2$ to $C_{12}$ alkylene-O—C(O)—C($CH_3$)=$CH_2$, —C(O)ONH—$C_2$ to $C_{12}$ alkylene-O—C(O)—CH=$CH_2$, or —C(O)NH—$C_2$ to $C_{12}$ alkylene-O—C(O)—C($CH_3$)=$CH_2$;

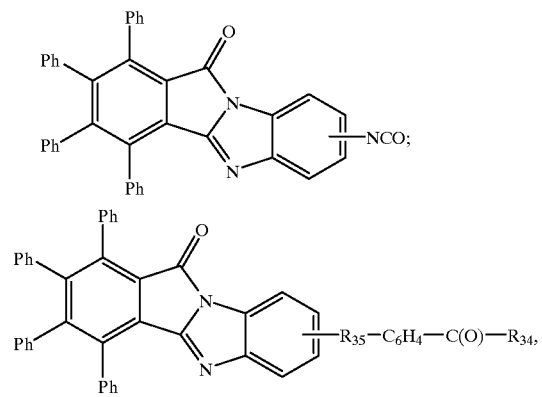

wherein $R_{35}$ is a direct bond, methylene, ethylidene, 2,2-propylidene, O, S, NH, N($C_1$ to $C_4$ alkyl), C(O) or C(O)NH, and $R_{34}$ has the meaning given before;

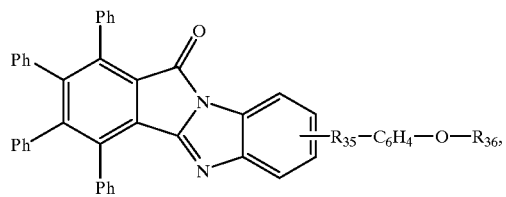

wherein $R_{35}$ has the meaning given before and $R_{36}$ means H, $C_2$ to $C_4$ hydroxyalkyl, glycidyl or $OR_{36}$ means NH-glycidyl or NH$C_2$ to $C_4$ hydroxyalkyl; and

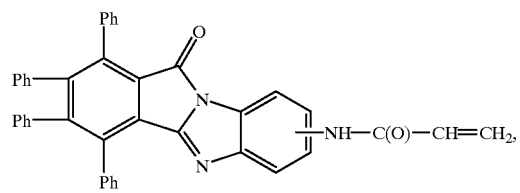

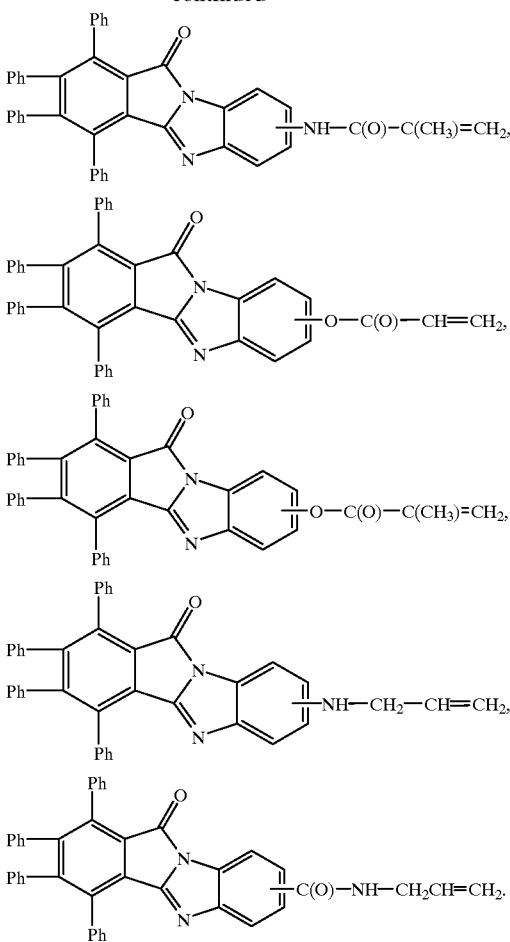

Preferred compounds of formula XXX correspond to the formulae XXXIII and XXXIIIa,

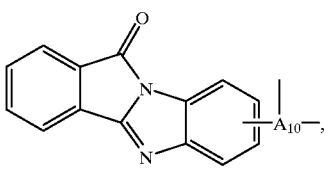 (XXXIII)

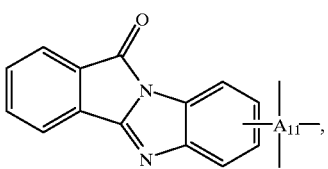 (XXXIIIa)

wherein
neighboring carbon atoms of the benzene ring can be condensed with benzene rings, heteroaromatic rings or both, and
the aromatic rings are unsubstituted or substituted with halogens like F, Cl or Br, —CN, —$NO_2$, $C_1$ to $C_{18}$ alkyl, $C_3$ to $C_{12}$ cycloalkyl, $C_6$ to $C_{18}$ aryl, $C_5$ to $C_{17}$ heteroaryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, $C_5$ to $C_{17}$ heteroaryloxy, $C_3$ to $C_{12}$ cycloalkylalkyloxy, $C_6$ to $C_{18}$ aralkyloxy, $C_5$ to $C_{17}$ heteroaralkyloxy, $C_1$ to $C_{18}$ alkylthio, $C_3$ to $C_{12}$ cycloalkylthio, $C_6$ to $C_{18}$ arylthio, $C_5$ to $C_{17}$ heteroarylthio, $C_3$ to $C_{12}$ cycloalkylalkylthio, $C_6$ to $C_{18}$ aralkylthio, $C_5$ to $C_{17}$ heteroaralkylthio, $C_1$ to $C_{18}$ alkyl-SO— or —$SO_2$, $C_3$ to $C_{12}$ cycloalkyl-SO— or —$SO_2$, $C_6$ to $C_{18}$ aryl-SO— or —$SO_2$, $C_5$ to $C_{17}$ heteroaryl-SO— or —$SO_2$, $C_3$ to $C_{12}$ cycloalkylalkyl-SO or —$SO_2$, $C_6$ to $C_{18}$ aralkyl-SO— or —$SO_2$, $C_5$ to $C_{17}$ heteroaralkyl-SO— or —$SO_2$, secundary amino with 2 to 30 carbon atoms, and alkoxyalkyl with 2 to 20 carbon atoms, the cyclic aliphatic and aromatic residues (substituents) may also be substituted, for example with halogens like F, Cl or Br; or —CN, —$NO_2$, $C_1$ to $C_{18}$ alkyl, $C_3$ to $C_{12}$ cycloalkyl, $C_6$ to $C_{18}$ aryl, $C_3$ to $C_{12}$ cycloalkylalkyl, $C_6$ to $C_{18}$ aralkyl, $C_5$ to $C_{17}$ heteroaralkyl, $C_1$ to $C_{18}$ alkyloxy, $C_3$ to $C_{12}$ cycloalkyloxy, $C_6$ to $C_{18}$ aryloxy, and $A_{10}$ means a trivalent and $A_{11}$ means tetravalent organic group.

Examples for substituents are F, Cl, Br, methyl, ethyl, propyl, butyl, hexyl, methyloxy, ethyloxy, propyloxy, butyloxy, hexyloxy, methylthio, ethylthio, methyl- or ethyl-SO—, methyl- or ethyl-$SO_2$—, phenyl, benzyl, toluyl, xylyl, methylbenzyl, dimethylbenzyl, chlorophenyl, dichlorophenyl, methoxyphenyl, dimethoxyphenyl, methoxybenzyl, dimethoxybenzyl.

Preferably the ring without the functional group is condensed with the neighboring carbon atoms to form bicyclic systems. They may be selected from benzene, furane, thiophene, pyrrole, pyridine, and pyrimidine.

In a preferred embodiment, $A_{10}$ corresponds to the formula XXXVI and $A_{11}$ corresponds to formula XXXVIa, $$—R_{31}—(X_4)_a—R_{32}—(X_8)_b \quad \text{(XXXIV)}$$

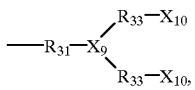 (XXXIVa)

wherein
(a) $R_{31}$ is a direct bond, $C_1$ to $C_{12}$ alkylene, phenylene or benzylene;
$X_4$ is N, O, S, C(O)O or C(O)N;
$R_{32}$ means $C_2$ to $C_{12}$ alkyltriyl, phenyltriyl or benztriyl, when a is 1 and b is 2, or means $C_2$ to $C_{12}$ alkyltetrayl, phenyltetrayl or benztetrayl, when a is 1 and b is 3;
$X_8$ means OH, SH, $NH_2$, C(O)OH, C(O)$NH_2$, OC(O)—CH=$CH_2$, OC(O)—C($CH_3$)=$CH_2$, HNC(O)—CH=$CH_2$, HNC(O)—C($CH_3$)=$CH_2$; or
(b) $R_{32}$ is a bond, a is 0 and b is 2 or 3, $X_8$ has the same meanings as above, and $R_{31}$ means $C_2$ to $C_{12}$ alkyltriyl, phenyltriyl or benztriyl, when b is 2, or means $C_2$ to $C_{12}$ alkyltetrayl, phenyltetrayl or benztetrayl, when b is 3;
(c) $R_{31}$ is a direct bond, $C_1$ to $C_{12}$ alkylene, phenylene or benzylene;
$X_9$ is N or C(O)N;
$R_{33}$ is $C_2$ to $C_{12}$ alkylene;
$X_{10}$ is OH, SH, C(O)OH, C(O)$NH_2$, or OC(O)—CH=$CH_2$, OC(O)—C($CH_3$)=$CH_2$, HNC(O)—CH=$CH_2$, HNC(O)—C($CH_3$)=$CH_2$ or —CH=$CH_2$.

$R_{31}$, and $R_{33}$, in the meaning of alkylene, contains preferably 2 to 8 and more preferably 2 to 4 C-atoms. $R_{32}$ in the meaning of alktriyl contains preferably 2 to 8, more preferred 2 to 6, and mostly preferred 2 to 4 C-atoms.

In a preferred embodiment the polyfunctional compounds correspond to formulae XXXV and XXXVa,

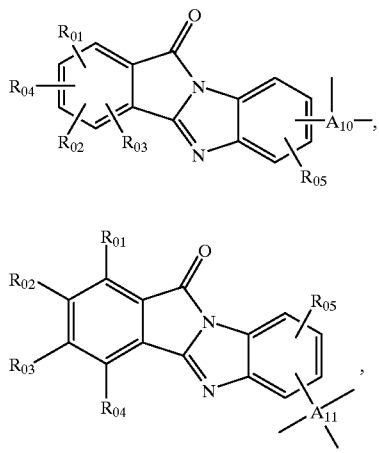
(XXXV)

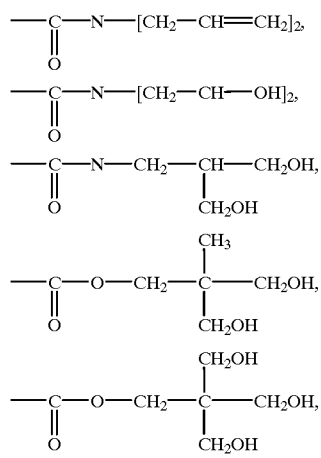
(XXXV)

wherein $R_{01}$, $R_{02}$, $R_{03}$, $R_{04}$, and $R_{05}$ independently from one another mean H, Cl, $C_1$ to $C_{18}$ alkyl, $C_1$ to $C_{18}$ alkoxy, phenyl, benzyl, $C_1$ to $C_{12}$ alkylphenyl or $C_1$ to $C_{12}$ alkylbenzyl, $A_{10}$ corresponds to formula XXXIV and $A_{11}$ corresponds to formula XXXIVa. $R_{05}$ means preferably H.

In a preferred embodiment the group $A_{10}$ and $A_{11}$ may be selected from the group

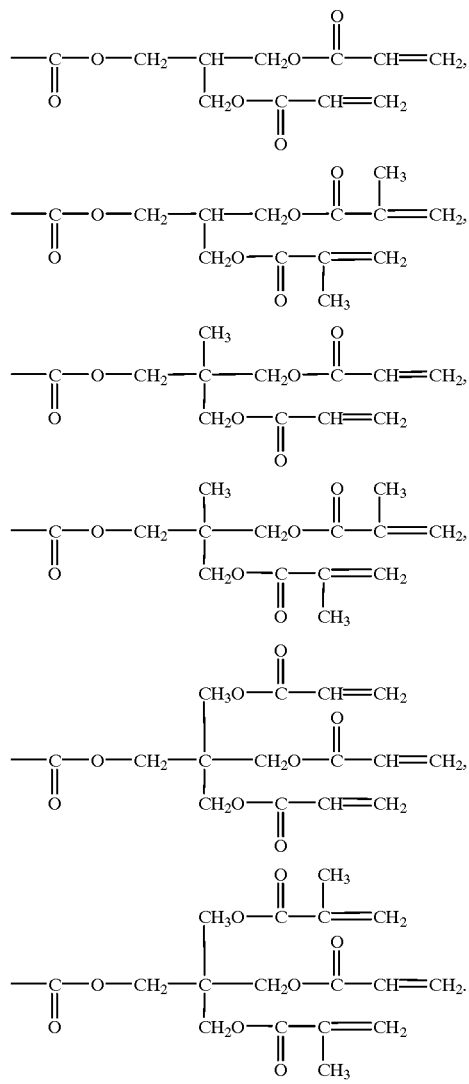

Some preferred examples of compounds of formulae XXXIII and XXXIIIa are compounds from the group (Ph means phenyl);

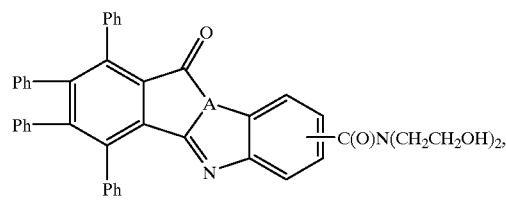

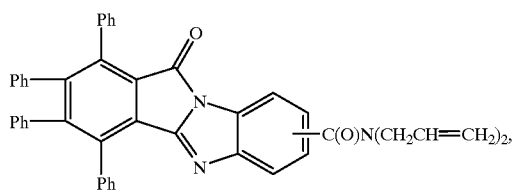

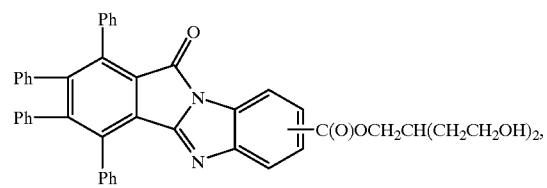

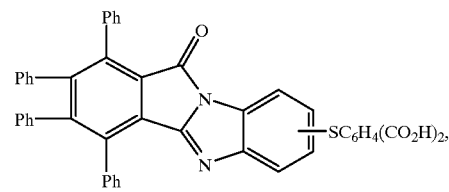

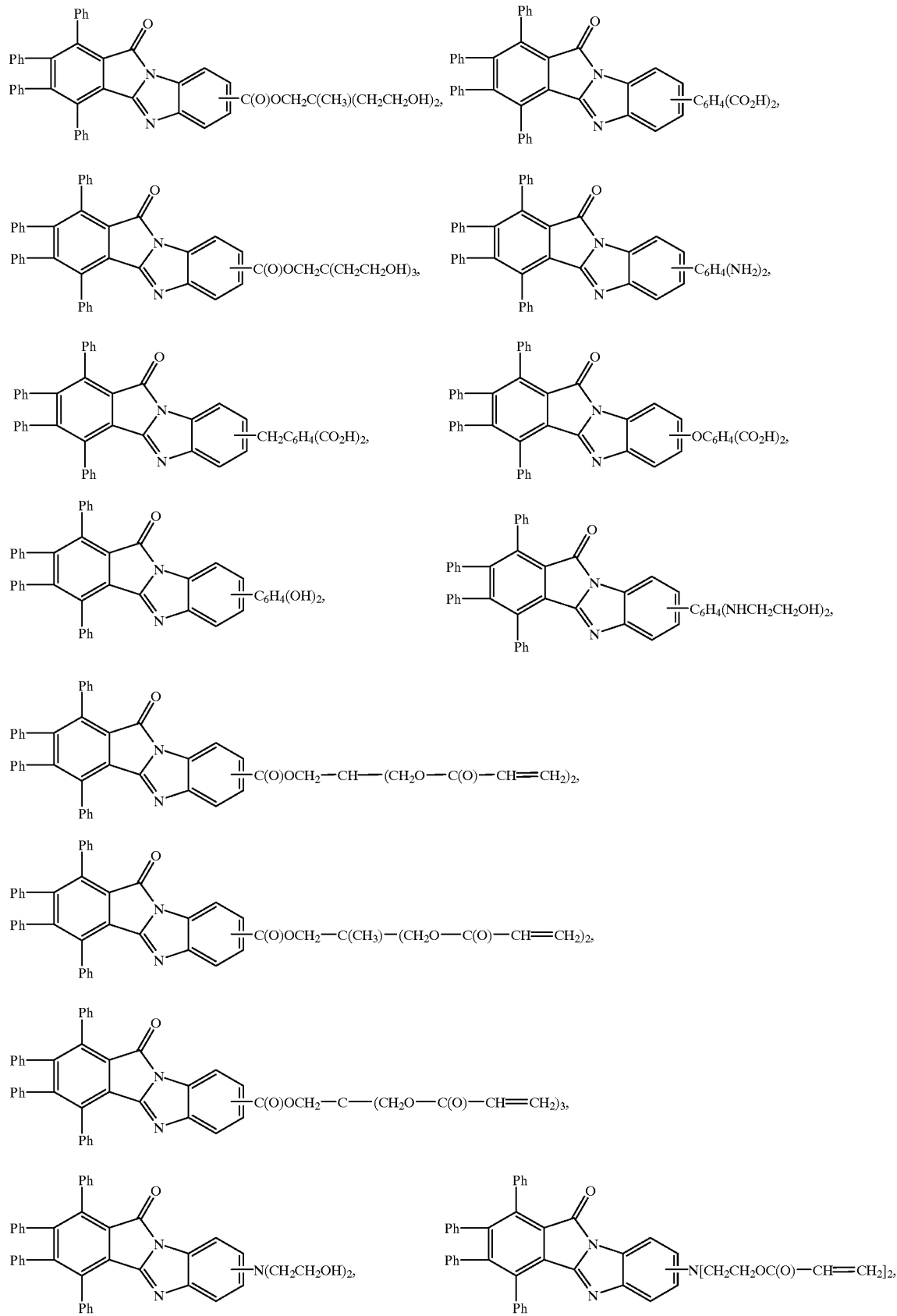

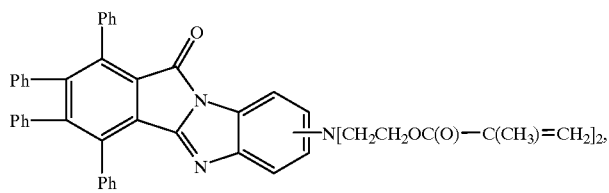

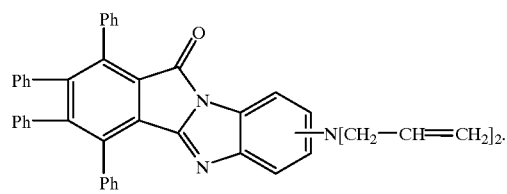

As examples for difunctional host compounds the following compounds may be mentioned:

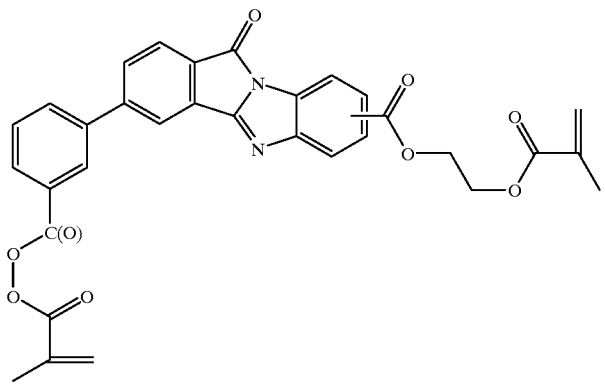

which may be synthesized starting from the corresponded acid chloride, for example by carrying out the reaction in a solvent like dry pyridine and thereby adding a, preferably large, excess of hydroxy ethyl methacrylate, preferably dissolved in the same solvent. Workup may be done by pouring the completed reaction mixture slowly on ice which may contain an acid like HCl, yielding a precipitate, which may be filtered and dried, for example by vacuum pumping. This crude precipitate preferably may be further purified, to remove residual hydroxyethyl methacrylate, by re-precipitation for example from chloroform into a large excess of hexane.

The corresponding acid chloride may be synthesized preferably reaction of the corresponding diacid compound with thionyl chloride, preferably in a solvent like dry benzene. The reaction mixture may be heated to complete the reaction, for example to reflux temperature. Solvent and excess thionyl chloride can be removed preferably using a stream of nitrogen.

The corresponding diacid compound may be synthesized for example starting from biphenyl-3,4,3' tricarboxylic acid, which is obtainable in accordance with the method described in Zh. Org. Khim 2(7), 1288 (1966), by reaction with 3,4-diamino benzoic, preferably in a solvent like acetic anhydride. The obtained benzo[4,5]-imidazo[2,1-a]isoindol-11-one-carboxylic diacid may be filtered and washed as usual with for example water and methanol, and may be further purified by column chromatography using preferably chloroform as the eluting solvent. (II)

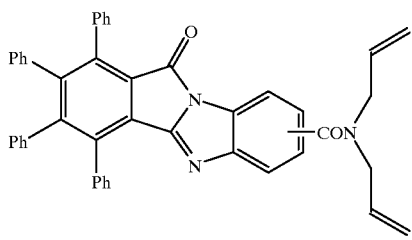

which may be synthesized starting from the corresponding tetrapheny-benzo[4,5]imidazo[2,1-a]isoindol-11-one-carboxylic acid chloride (obtainable in a similar manner as the abovementioned diacid chloride) by reaction with diallylamine, preferably dissolved in a solvent like dry pyridine. Workup may be carried out by pouring the reaction mixture in ice cold water, washing the obtained crude reaction product with water and dried it. Further purification may be done via column chromatography using for example chloroform as the eluting solvent.

As an example for a trifunctional host compound the following compound may be manufactured:

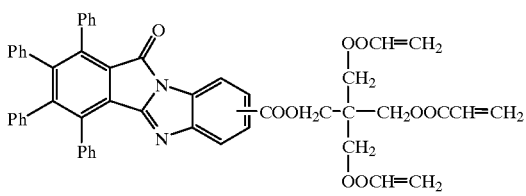

The preparation of this compound may be carried out starting from the corresponding tri-functional OH-derivative of tetraphenyl-benzo[4,5]imidazo[2,1-a]isoindol-11-one with acryloylchloride, preferably in a solvent like dichloromethane. Workup may be carried out in pouring the reaction mixture in a large excess of water, followed by filtering the obtained precipitate. If desired the crude product may be washed further for example with water and methanol and then dried, for example in an atmosphere under reduced pressure. The corresponding trifunctional OH-derivative may be synthesized preferably by the reaction of pentaerythritol (large excess) with tetraphenyl-benzo[4,5]imidazo[2,1-a]isoindol-11-one-carboxylic acid chloride (obtainable by reaction of the corresponding carboxylic acid with thionyl chloride), preferably in a solvent like dry pyridine. Workup may be carried out as usual and described before.

The process to prepare the materials and compounds according to the invention usually can be carried out in an inert solvent. Inert means that there will be undesired side reactions between the ingredients and the solvent. Solvents may also be applied when employing materials according to the invention.

Suitable inert solvents are for example protic-polar and aprotic solvents, which may be used alone or in an admixture of at least two solvents. Examples are: water, alcohols (methanol, ethanol, propanol, butanol), ethyleneglycolmonomethyl- or -monoethylether, ether (dibutylether, tetrahydrofuran, dioxane, ethyleneglycol dimethylether, ethyleneglycoldiethylether, diethyleneglycoldiethylether, triethyleneglycoldimethylether), halogenated hydrocarbons (methylenchloride, chloroform, 1,2-dichloroethane, 1,1,1-trichlororethane, 1,1,2,2-tetrachloroethane), carboxylic esters and lactones (acetic acid ethylester, propionic acid methylester, benzoic acid ethylester, 2-methoxyethylacetate, γ-butyrolactone, δ-valerolactone, pivalolactone), carboxylic acid amides and lactames; N,N-dimethylformamide, N,N-diethylformamide, N, N-dimethylacetamide, tetramethylurea, hexamethylphosphorous acidtriamide, γ-butyrolactame, ε-caprolactame, N-methylpyrrolidone, N-acetylpyrrolidone, N-methylcaprolactame; sulfoxides (dimethylsulfoxide), sulfones (dimethylsulfone, diethylsulfone, trimethylenesulfone, tetramethylenesulfone), tertiary amines (N-methylpiperidine, N-methylmorpholine), aliphatic and aromatic hydrocarbons like petroleumether, pentane, hexane, cyclohexane, methylcyclohexane, benzene or substituted benzenes (chlorobenzol, o-dichlorobenzene, 1,2,4-trichlorobenzene, nitrobenzene, toluene, xylene) and nitriles (acetonitrile, propionitrile, benzenenitrile, phenylacetonitrile), ketones (acetone, methyl-isobutyle-ketone).

The compound 1,2,3,4-tetraphenyl- benzo[4,5]imidazo[2,1-a]isoindol-11-one and its derivatives, which are a preferred group of host compounds used in this invention, possess an absorption maximum at around 370 nm, which lies in the UV region. However, their excitation wavelengths stretch from around 350 nm, in the UV, to 450 nm, in the visible region of the electromagnetic spectrum. Consequently, host/guest type materials employing this class of compounds, as a host, can span a broad number of applications as they readily facilitate themselves to excitation by both UV and daylight radiation sources. Therefore, these materials could be rendered very useful as coloring agents in applications such as road markings and traffic signs for night and daylight uses, as they exhibit brilliant daylight fluorescence and can also be excited by the UV radiation of motor vehicles halogen lamps, thereby providing intense, bright colors during both day and nighttime. Other applications include their use as pigments, coloring agents, materials for scintillators, materials for solar energy collectors, materials for light emitting electroluminescent devices, materials for generating fluorescent images as well as in printing inks. Moreover, the choice of guest compound can lend a lot of flexibility to the desired emission wavelength required of the overall system, therein imparting the capability for color-tuning and ease of tailoring of the core system to specific color applications via wavelength modulation. It is also possible to produce fluorescent images (high relief structures) by the well known photoresist technology. The compositions of the invention may also be used in paintings, lacquers or printing inks.

The compositions according to the invention may be used in various forms depending upon the end-use purpose:

The polymers of completion form (A) may be milled or can be produced in the form of particles. A further preferred embodiment of the invention is a polymer according to the completion form (A) in the form of particles, especially finely divided particles.

The average diameter or particle size may correspond to that of the particles according to completion form (B).

The polymers according to the invention may be admixed with other polymers i.e. a further preferred embodiment of the invention is a composition containing (a) a blend of a non-fluorescent polymer substrate and (b) a polymer according to the completion form (A).

The amount of component (b) may be for example from 0.1 to 99.9 percent by weight, preferably 1.0 to 50 percent by weight with respect to the total composition. The amount used depends essentially from the amount of host and guest structural units in the polymer of completion form (A) and also upon the compatibility with the polymer substrate.

The polymers may be selected from thermoplastics, thermosettings and structurally crosslinked polymers. The admixture of thermoplastics with thermoplastics of completion form (A) are polymeric alloys. The polymers may be homopolymers, copolymers, blockpolymers, graft polymers or random polymers.

The polymers may be opaque or translucent, but preferably transparent. The polymers may be selected for example from the group of thermoplastic polymers like polyesters, polyamides, polyimides, polyamide-imides, polyamide esters, polyurethanes, polyureas, polyolefines; polymers from substituted olefines like vinylethers, vinylesters, vinylalcohols, vinylchloride, vinyldichloride, acetonitrile, acrylic acid, methacrylic acid, esters and amides of acrylic acid and methacrylic acid, styrene, chlorostyrene, methylstyrene, styrene sulfonic acid and their esters and amides, vinylcarbazole, vinylpyridine, vinylpyrrolidone: polymaleic acid and esters and amides therefrom; polyethers, polysufones, polyketones, polyphenylsulfides, and polyacetales; cellulose and its esters and ethers, and starch or derivatives of starch.

Examples of thermosetting resins and structurally crosslinked resins are polyepoxides, unsaturated polyesters, photocrosslinked resins for example from acrylic acid and/or methacrylic esters and/or amides from polyols and/or polyamines, melamine/formaldehyde resins, and phenol/formaldehyde resins; polymers from butadiene, isoprene and or chloroprene and copolymers with olefins, which may be crosslinked and of rubbery nature; as well as silicates obtainable for example through the known sol/gel process.

The thermoplastic compositions are for example obtainable by known mixing methods like admixing solutions of polymers and removing the solvent, injection molding and extrusion molding. Thermosetting and structurally crosslinked compositions are obtainable by known methods like press molding, whereby the polymer of completion form (A) which is preferably of low molecular weight, is dissolved in the polymerisable mixture.

It is also a further aspect of the invention that the polymer of completion form (A) may be mixed with non-fluorescent crosslinking units, such as multi-functional monomers or prepolymers and crosslinked together to generate semi-interpenetrating networks.

In a further aspect the polymer particles of completion form (B) or completion form (A) or both together may be used as filler for thermoplastic, thermosetting and structurally crosslinked polymers.

A further preferred embodiment of the invention is a composition comprising (a) a polymer substrate, and (b) particles of the completion form (B), polymer particles of a polymer according to the completion form (A) or both uniformly distributed therein.

The amount of the particles may be for example 0.01 to 90 weight %, preferably 0.1 to 90 weight % and more preferably 1 to 50 weight % of the total composition.

The polymer substrate may include those as described above. This composition can be easily prepared by known mixing methods as described above, whereby the particles are dispersed prior to the polymerization of a precursor composition.

The polymeric compositions of the invention may contain further ingredients to enhance certain features such as electrical, physical and mechanical properties, and/or the processability; for example dispersing agents to achieve a uniform distribution of particles, lubricants, plasticizers, antistatica, solvents, molding agents, antioxidants, light stabilizers, fillers and reinforcing fillers like glass balls and glass fibbers, silicates (e.g. mica, clay, wollastonite), metal and semiconductor metal oxides, metal carbonates, metal salts, metals and semiconductor metals, carbon black, as powder, or carbon fibers, whiskers, metal and semiconductor metal carbides, metal and semiconductor metal nitrides, dyes, pigments and others.

The compositions of the invention me be used in the form of shaped articles, including the surface modified compositions of completion form (B).

A further preferred embodiment of the invention is therefore a shaped article from (a) the composition according to the polymers of completion form (A), or (b) a composition of (b1) a polymer substrate containing either (b2) polymers according to the completion form (A), or (b3) particles of the polymers of completion form (A), of the completion form (B) or both, alone or together with a polymer of the completion form (A), which are uniformly distributed in the said polymer substrate.

In another aspect the polymers and particles of the completion form (A) or the particles of the completion form (B) may be used as coatings on carrier materials, using the above mentioned compositions.

Another object of the invention is a composition comprising (a) a carrier material and (b) at least on one surface a coating of;

(1) a polymer of completion form (A),
(2) a polymer substrate containing uniformly distributed particles of the completion form (A), completion form (B) or both, or (3) a polymer mixture comprising a substrate polymer and in uniform distribution a soluble polymer of completion form (A) and in admixture particles of the completion form (A), completion form (B) or both.

Suitable carrier materials may be selected from organic or inorganic materials like glass, ceramics, minerals, plastics, paper, wood, semiconductors, metals, metal oxides and semiconductor metal oxides, and metal or semiconductor metalnitrides or -carbides.

The thickness of the coating depends on the desired use and may be from 0.1 to 1000 $\mu$m, preferably 0.5 to 500 $\mu$m, and especially preferred 1 to 100 $\mu$m.

The coatings may be protected by covering coatings which are preferably transparent. Such coatings are well known, and in general photocrosslinked coatings are mainly used for this purpose. Moreover, the materials belonging to completion form (A), which are surface modified, may also be protected by coatings.

The coated materials are obtainable by known methods such as painting, casting or spincoating, directly or with a solution or dispersion of the polymeric compositions. It is also possible to use a polymerisable composition containing polymer forming monomers, especially crosslinkable olefinically unsaturated monomers. The polymerization may be induced thermally or by actinic radiation. The coating compositions are novel and a further preferred embodiment of the invention.

A further preferred embodiment of the invention is therefore a liquid and a solvent containing a composition, comprising;

(1) a polymer of completion form (A), and optionally a nonfluorescent polymer,
(2) a polymer substrate containing uniformly dispersed particles of the completion form (A),
(3) or both, alone or in admixture with a soluble polymer of completion form (A).

These compositions may contain a solvent, such as those mentioned before, and optionally surfactants and dispersing agents. The viscosity range depends on the desired application for the coating, wherein the desired viscosity can be achieved by choice of solvent and polymer quantity. To further aid achieving a desired viscosity thickening agents may additionally be used. Again suitable solvents have been mentioned previously.

The preparation of this composition can be achieved by simply mixing the ingredients together using suitable mixing equipment. Dispersions are in general stable depending upon the viscosity. If particles should aggregate they may be redistributed by stirring.

In a highly advantageous embodiment of preparing coatings polymerisable compositions can be used, wherein at least one surface of a carrier material is coated and subsequently polymerized by heat or radiation. Photopolymerizable mixtures can also be used to generate fluorescent images by known photoresist technology.

A further preferred embodiment of the invention is a polymerisable composition comprising a) polymerisable monomers or prepolymers in admixture with particles of completion forms (A), (B) or both, and optionally dissolved therein a polymer according to completion form (A); b) polymerisable monomers or prepolymers and dissolved therein a polymer according to completion form (A); or c) a polymerisable host containing at least one polymerisable group or at least two functional groups or a prepolymer of it, a polymerisable guest chromophore containing at least one polymerisable group or at least two functional groups copolymerisable with that of the host compound or a prepolymer of it, and optionally nonfluorescent monomers or prepolymers copolymerisable with both that of the host compound and that of the guest chromophore.

The composition may be used to generate the polymers of completion form (A) as described before. When coatings or images are to be generated, the composition preferably contains a solvent. The afore described embodiments also apply to this composition, inclusive of the preferred embodiments.

In a preferred embodiment the composition is based on polymerisable monomers and/or prepolymers containing a group selected from olefinically unsaturated groups, preferably from —CH═CH$_2$ and —C(CH$_3$)═CH$_2$, which can be thermally or photo-polymerized.

Photopolymerisable monomers and prepolymers are well known in the art and described for example in EP-A-0 654 711. Preferred photopolymerisable monomers and prepolymers are those based on the esters or amides of acrylic acid or methacrylic acid and alcohols, polyols, amines and polyamines.

The photopolymerisable composition is particularly suitable to generating coatings and images.

A further preferred embodiment of the invention is a composition comprising of (a) a carrier material, to which on at least one of its surfaces is (b) a high relief image of a polymerized photoresist material, which contains
(b1) particles of completion forms (A), (B) or both in uniform distribution, and optionally dissolved therein a polymer according to completion form (A);
(b2) uniformly distributed therein a polymer according to completion form (B); or
(b3) a polymer from a photopolymerisable host containing at least one polymerisable group or at least two functional photoreactive groups or a prepolymer of it, from a guest chromophore containing at least one photopolymerisable group or at least two photoreactive functional groups or a prepolymer of it copolymerisable with that of the host compound, and optionally monomers or prepolymers copolymerisable by irradiation with both that of the host compound and that of the guest chromophore.

A further preferred embodiment of the invention is a process for the preparation of fluorescent high relief images on a carrier. This involves irradiating under a mask or by laser writing, the above coated photopolymerisable composition (which has been dried and removed of solvent) on the carrier, developing the irradiated composition and finally removing the non-irradiated parts.

Removal of the non-irradiated parts is mostly carried out by treatment with solvent.

All the materials described before are highly fluorescent materials which can broadly be used in optical and electroptical devices according to observations hitherto.

A further preferred embodiment of the invention is a process for the creation of fluorescent radiation which requires the excitation either electrically or by UV or visible radiation, or both, of a fluorescent composition according to the invention.

Another preferred embodiment of this invention is the use of the compositions according to the invention as fluorescent materials.

The following examples demonstrate the invention.
A) Preparation of Host-Monomer/Polymer Intermediates.

EXAMPLE A1

1,2,3,4tetraphenyl-benzo[4,5]imidazo[2,1-a] isoindol-11-one-7-carboxylic acid (A1, inclusive the 8-isomer)

Into a reaction vessel equipped with a condenser, light nitrogen purge and magnetic stirrer, 10 g (0.022 mol) of tetraphenylphthalic anhydride and 3.35 g (0.022 mol) of 3,4 diaminobenzoic acid are added, along with 100 ml of acetic acid. The gray colored reaction mixture is heated to reflux temperature. After several hours the reaction begins to take-on a dark yellow color. The reaction mixture is then left for a further 72 hours at slightly below reflux temperature (105° C.).

The bright yellow precipitate is filtered and washed with water and methanol. The yellow product is then left to dry at the water aspirator before final drying in a vacuum oven overnight (60° C.). The obtained yield is 81%.

EXAMPLE A2

1,2,3,4tetraphenyl-benzo[4,5]imidazo[2,1-a] isoindol-11-one-7(or 8)carboxylic acid chloride (A2, inclusive the 8-isomer)

Into a reaction vessel equipped with a condenser, light nitrogen purge and magnetic stirrer, 5 g (0.0088 mol) of compound A1 and 30 ml of dry benzene are added. Keeping at room temperature, a molar excess of thionyl chloride is added to the reaction mixture, which is then allowed to stir for 30 minutes. The reaction mixture, which is a yellow suspension, is then heated to reflux temperature for about 2 hours, to yield a clear golden colored solution. The solvent and excess thionyl chloride are removed using a stream of nitrogen, to furnish the yellow acid chloride derivative. The yield is 94%.

B) Preparation of Functionalized Host Derivatives

EXAMPLE B1

1,2,3,4tetraphenyl-benzo[4,5]imidazo[2,1-a] isoindol-11-one-7-carboxy ethyl methacrylate (B1, inclusive the 8-isomer)

4 g of A2, dissolved in 30 ml of dry pyridine are added slowly over the period of about 30 minutes, to a stirred solution containing 5 g (large excess) hydroxy ethyl methacrylate in 10 ml of dry pyridine at room temperature. The reaction mixture is left at room temperature to stir for a further 2 hours.

The completed reaction mixture is then slowly added, with stirring, to a beaker containing 100 g of ice and 100 ml of 1M HCl. A yellow precipitate is obtained and allowed to settle before filtration (sinter glass G3), to yield the crude product. The crude precipitate is further purified, to remove residual hydroxyethyl methacrylate, by re-precipitation from chloroform into a large excess of hexane (Yield 86%).

C.) Preparation of Functionalized Guest Compounds.

EXAMPLE C1

Carboxy ethyl methacrylate derivative of Rhodamine-B (C1) Into a reaction vessel equipped with a condenser, light nitrogen purge and magnetic stirrer 3.5 g (0.0073 mol) of rhodamine-B are added to about 30 ml of anhydrous dichloromethane (Aldrich Special Grade). Whilst keeping at room temperature 1.54 g (0.0095 mol, 1.3 excess) of N.N'-carbonyl diimidazole is added over the period of about 10 minutes to the vigorously stirred rhodamine solution. This reaction is left to stir for a further 4 hours at room temperature to afford the desired acid imidazole.

A three times equivalent amount of 2-hydroxyethyl methacrylate (2.8 g, 0.022 mol) is then added to the reaction mixture and allowed to stir for a further 72 hours at room temperature. The solvent is removed from the crude reaction mixture, and the product purified by column chromatography. 90CHCl$_3$/10MeOH is employed as the eluting solvent.

EXAMPLE C2

Preparation of multifunctional diketopyrrolopyrole compounds similar to C2 below can be achieved by methods described in EP 0 337 951, or, more specifically, in analogy to EP-A 787 731 (esp. example 12 described therein):

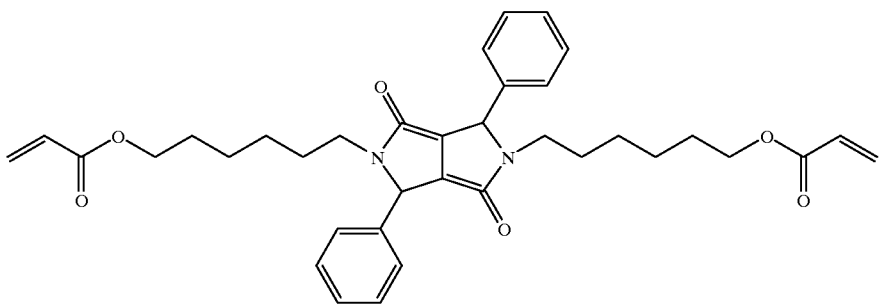

(C2)

EXAMPLE C3

Preparation of N,N'-di-vinylbenzyl quinacridone Under an atmosphere of nitrogen 1.6 g of potassium-tert.-butoxide are added over a period of about 40 min to a mixture of 200 ml dimethylformamide ("DMF") and 4 g of finely divided quinacridone, and the whole reaction mixture is allowed to stir for a further 20 min. Them, a large excess of vinyl benzyl chloride (4 g) is slowly added over about 30 min affording a dark green solution, which is left at room temperature overnight. Afterwards, the reaction mixture is poured into vigorously stirred water affording a bright orange precipitate. After drying, the orange precipitate is purified by column chromatography, employing dichloromethane as the eluting phase.

D) Preparation of Fluorescent Polymers.

EXAMPLE D1

Into a 10 ml reaction flask (cleaned using chromic acid), 0.0142 g of guest monomer (C2) is placed and dissolved in 1.5 ml of chloroform. 1 g of the host monomer (B1) is then added along with a further 2.0 ml of chloroform, and 0.005 g of recrystallized azobisisobutyronitrile (AIBN) to act as initiator. The reaction solution is then removed of dissolved oxygen, by bubbling with nitrogen gas for 30 minutes. The reaction mixture is then polymerized in a water bath at 60° C. and terminated when the viscosity of the reaction mixture increased sufficiently (1 hour). The polymer is purified by a series of reprecipitation from toluene (or chloroform) into methanol. Yield: 40%. $M_w=2.10^5$ g/mol.

EXAMPLE D2

Into a 10 ml reaction flask (cleaned with chromic acid), 0.6366 g of B1, 0.3970 g of methyl methacrylate and 0.0142 g of C2 are added. The monomer mixture is dissolved in 3 ml of chloroform and 0.0052 g of recrystallized AIBN is added as initiator. The reaction feed mixture is degassed by bubbling dry nitrogen through the solution for 30 minutes. The reaction mixture is placed in a water bath at 60° C. and polymerization reaction terminated when the viscosity of the solution increased sufficiently (2 hours). The polymer is isolated by precipitation into methanol and purified by a series of reprecipitations. Yield 25%. $M_w=2.5.10^5$ g/mol.

EXAMPLE D3

A comonomer solution of 0.74 g B1, 0.01 C2, 0.71 g of ethylene glycol dimethacrylate and 0.029 g of AIBN dissolved in 1.8 g of chloroform is added to a vigorously stirred solution of water at 60C. After 8 hours highly fluorescent, highly crosslinked insoluble particles are yielded. Yield 80%.

EXAMPLE D4

5.5 g of purified polymer (the mol % composition of which is approximately 70 methyl methacrylate/30 hydroxy ethyl methacrylate) is dissolved in 150 ml of dry pyridine and kept under a nitrogen atmosphere at room temperature. To the stirred polymer solution a mixture of 0.01 mol (5.86 g) of B1 and 0.00004 mol (0.0227 g) of the carboxylic acid chloride derivative of Rhodamine-B, in 50 ml of dry pyridine are added over the period of 1 hour. After stirring at room temperature for 4 hours the reaction mixture is heated to 60° C. for a further 12 hours. Upon cooling, the reaction mixture is three times precipitated into a large excess of methanol. Before final drying, the precipitated polymer is thoroughly washed with water and methanol to remove any unreacted rhodamine monomer.

EXAMPLE D5

Into a 10 ml reaction flask (cleaned using chromic acid), 0.9735 g of host monomer B1 is placed and dissolved in 1.5 ml of chloroform. 0.0025 g of the guest monomer C3 is then added along with a further 2.0 ml of chloroform, and 0.006 g of recrystallized azobisisobutyronitrile (AIBN) to act as initiator. The reaction solution is then removed of dissolved oxygen, by bubbling with nitrogen gas for 20 minutes. The reaction mixture is then polymerized in a water bath at 60° C. and terminated when the viscosity of the reaction mixture increased sufficiently (33 min). The polymer is purified by a series of reprecipitation from toluene (or chloroform) into methanol. Yield: 33%. $M_w=1.2.10^5$ g/mol.

E) Preparation of Fluorescent Coated Support Materials

It is possible to prepare thin film devices comprising non-crosslinked compositions of the present invention by dissolving the material in a suitable solvent, the weight-volume (w/v) percent of which is dependent on the desired film thickness and the end application, but is usually in the range 0.01 to 30 w/v %. The above solution can then be coated onto the desired substrate by techniques which are well known to those familiar with the art.

F) Application Examples

EXAMPLE F1

Photoluminescence and excitation spectra of all fluorescent polymer samples are recorded using a Hitachi F-4500 Fluorescence Spectrophotometer in the standard reflectance mode, with the aid of a commercial solid sampler that possesses a transparent quartz window. All polymer samples are ground into fine powders, via a standard laboratory mortar and pestle, and uniformly packed into the sample holder. The monochromatic excitation wavelength is 365 nm and the scan rate 240 nm/min. The measured emission wavelength for various polymeric systems are detailed in Table 1.

TABLE 1

| Example | Polymer Feed Ratios (wt %) | | | Emission max(nm) | Intensity Arb. Units | (nm) |
|---|---|---|---|---|---|---|
| | Host | Guest | Other | | | |
| D1 | B1 (99 wt %) | C2 (1 wt %) | — | 543 | 2594 | 178 |
| D2 | B1 (61 wt %) | C2 (1 wt %) | mma (38 wt %) | 538 | 2947 | 173 |
| D3 | B1 (49 wt %) | C2 (1 wt %) | EGDM* (50 wt %) | 557 | 2240 | 192 |
| D4 | A2 (52 wt %) | Rhodamine B (0.2 wt %) | — | 583 | 2390 | 218 |

*EGDM: ethylene glycol dimethacrylate: mma: methylmethacrylate

What is claimed is:

1. A composition comprising a solid organic support material to which either directly or via a bridging group, are covalently linked fluorescent host chromophores and fluorescent guest chromophores, wherein the fluorescence emission spectrum of the host chromophore overlaps with the absorption spectrum of the guest chromophore, wherein the host chromophore is selected from the group consisting of benzo[4,5]imidazo[2,1-a]isoindol-11-ones.

2. A composition according to claim 1, characterized in that the support material is selected from the group consisting of linear or crosslinked polymers with pendent host and guest structures, and surface modified polymers containing pendent host and guest structures on their surfaces.

3. A composition according to claim 2, characterized in that it comprises a completion form (A) consisting essentially of polymers with host and guest molecules, which are either directly, or via a bridging group, covalently linked to the backbones of the polymers.

4. A composition according to claim 2, characterized in that it comprises a completion form (B) consisting essentially of organic support materials to which host and guest molecules are either directly or via a bridging group covalently linked to the surfaces of said support materials.

5. A composition, characterized in that it represents (a) a blend of a non-fluorescent polymer substrate and (b) a polymer according to a completion form (A) consisting essentially of polymers with host and guest molecules, which are either directly, or via a bridging group, covalently linked to the backbones of the polymers.

6. A composition, characterized in that it comprises (a) a polymer substrate, and (b) particles of a completion form (B) consisting essentially of organic support materials to which host and guest molecules are either directly or via a bridging group covalently linked to the surfaces of said support materials, polymer particles of a polymer according to a completion form (A) consisting essentially of polymers with host and guest molecules, which are either directly, or via a bridging group, covalently linked to the backbones of the polymers or both uniformly distributed therein.

7. A composition comprising (a) a carrier material and (b) to at least on one of its surfaces is applied a coating of;

(1) a polymer of a completion form (A) consisting essentially of polymers with host and guest molecules, which are either directly, or via a bridging group, covalently linked to the backbones of the polymers, (2) a polymer substrate containing uniformly distributed particles of the completion form (A), a completion form (B) consisting essentially of organic support materials to which host and guest molecules are either directly or via a bridging group covalently linked to the surfaces of said support materials, or both, or (3) a polymer mixture comprising a substrate polymer and in uniform distribution a soluble polymer of completion form (A) and in admixture particles of the completion form (A), completion form (B) or both.

8. A polymerisable composition comprising;

a) polymerisable monomers or prepolymers in admixture with particles of a completion form (A) consisting essentially of polymers with host and guest molecules, which are either directly, or via a bridging group, covalently linked to the backbones of the polymers, a completion form (B) consisting essentially of organic support materials to which host and guest molecules are either directly or via a bridging group covalently linked to the surfaces of said support materials, or both, and optionally dissolved therein a polymer according to completion form (A);

b) polymerisable monomers or prepolymers and dissolved therein a polymer according to completion form (A); or c) a polymerisable host containing at least one polymerisable group or at least two functional groups or a prepolymer of it, a polymerisable guest chromophore containing at least one polymerisable group or at least two functional groups copolymerisable with that of the host compound or a prepolymer of it, and optionally non-fluorescent comonomers or prepolymers copolymerisable with both that of the host compound and that of the guest chromophore.

* * * * *